US012807929B2

(12) United States Patent
Sullivan et al.

(10) Patent No.: US 12,807,929 B2
(45) Date of Patent: Nov. 24, 2026

(54) ARTIFICAL LIVER ORGANOIDS AND METHODS OF THEIR PRODUCTION

(71) Applicants: Oslo Universitetssykehus HF, Oslo (NO); Universitetet i Oslo, Oslo (NO)

(72) Inventors: Gareth J. Sullivan, Eidsvoll Verk (NO); Sean Harrison, Oslo (NO); Richard Siller, Worcester, MA (US)

(73) Assignees: Oslo Universitetssykehus HF, Oslo (NO); Universitetet i Oslo, Oslo (NO)

( * ) Notice: Subject to any disclaimer, the term of this patent is extended or adjusted under 35 U.S.C. 154(b) by 792 days.

(21) Appl. No.: 18/026,477

(22) PCT Filed: Nov. 11, 2021

(86) PCT No.: PCT/IB2021/000781

§ 371 (c)(1),
(2) Date: Mar. 15, 2023

(87) PCT Pub. No.: WO2022/101675

PCT Pub. Date: May 19, 2022

(65) Prior Publication Data

US 2023/0399623 A1 Dec. 14, 2023

Related U.S. Application Data

(60) Provisional application No. 63/113,287, filed on Nov. 13, 2020.

(51) Int. Cl.
*C12N 5/071* (2010.01)
*A61K 35/407* (2015.01)

(52) U.S. Cl.
CPC .......... *C12N 5/0671* (2013.01); *A61K 35/407* (2013.01); *C12N 2501/12* (2013.01); *C12N 2501/33* (2013.01); *C12N 2501/39* (2013.01); *C12N 2501/415* (2013.01); *C12N 2501/727* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 2017/0191030 A1 | 7/2017 | Huch Ortega et al. | |
| 2018/0258400 A1 | 9/2018 | Ng et al. | |
| 2020/0199537 A1 | 6/2020 | Takebe et al. | |

FOREIGN PATENT DOCUMENTS

| | | | |
|---|---|---|---|
| WO | WO-2017048193 A1 * | 3/2017 | .......... C12N 5/0679 |
| WO | WO 2019/185017 | 10/2019 | |
| WO | WO 2020/056158 | 3/2020 | |

OTHER PUBLICATIONS

Davis et al. Automated Closed-System Expansion of Pluripotent Stem Cell Aggregates in a Rocking-Motion Bioreactor. SLAS Technol. Aug. 2018;23(4):364-373.Epub Feb. 26, 2018. (Year: 2018).*

MacParland et al. Single cell RNA sequencing of human liver reveals distinct intrahepatic macrophage populations. Nat Commun. Oct. 22, 2018;9(1):4383. (Year: 2018).*

Meyer et al. Contribution of human esterases to the metabolism of selected drugs of abuse. Toxicol Lett. Jan. 5, 2015;232(1):159-66. Epub Oct. 24, 2014. (Year: 2014).*

Hamoud et al. Bilirubin in the Liver to Gut Signaling Axis. Trends Endocrinol Metab. Mar. 2018;29(3):140-150. Epub Feb. 3, 2018. (Year: 2018).*

Pettinato et al. Generation of fully functional hepatocyte-like organoids from human induced pluripotent stem cells mixed with Endothelial Cells. Sci Rep. Jun. 20, 2019;9(1):8920. (Year: 2019).*

International Search Report & Written Opinion, International Patent Application No. PCT/IB2021/000781, dated Feb. 23, 2022, 15 pages.

Harrison, S. et al. "Liver Organoids: Recent Developments, Limitations and Potential", Frontiers in Medicine, vol. 8, May 5, 2021, 18 pages XP055887976.

Harrison, S. et al. "Scalable production of tissue-like vascularised liver organoids from human PSCs" bioRxiv, Dec. 2, 2020, XP055887988, retrieved from the internet: www.researchgate/net/publication/346628396_Scalable_production_of_tissue-like_vascularised_liver_organoids_from_human_PSCs#fullTextFileContent [retrieved on Feb. 7, 2022] 32 pages.

Trefts, E., Gannon, M. & Wasserman, D.H. The liver. *Curr Biol* 27, R1147-R1151 (2017).

Yin, X. et al. Engineering Stem Cell Organoids. *Cell Stem Cell* 18, 25-38 (2016).

Sullivan, G.J. et al. Generation of functional human hepatic endoderm from human induced pluripotent stem cells. *Hepatology* 51, 329-335 (2010).

Mathapati, S. et al. Small-Molecule-Directed Hepatocyte-Like Cell Differentiation of Human Pluripotent Stem Cells. *Current Protocols in Stem Cell Biology* 38, 1G.6.1-1G.6.18, 18 pages (2016).

Siller, R., Greenhough, S., Naumovska, E. & Sullivan, G.J. Small-molecule-driven hepatocyte differentiation of human pluripotent stem cells. *Stem Cell Reports* 4, 939-952 (2015).

Asahina, K., Zhou, B., Pu, W.T. & Tsukamoto, H. Septum transversum-derived mesothelium gives rise to hepatic stellate cells and perivascular mesenchymal cells in developing mouse liver. *Hepatology* 53, 983-995 (2011).

Li, Y., Wang, J. & Asahina, K. Mesothelial cells give rise to hepatic stellate cells and myofibroblasts via mesothelial-mesenchymal transition in liver injury. *Proc Natl Acad Sci U S A* 110, 2324-2329 (2013).

Matsumoto, K., Yoshitomi, H., Rossant, J. & Zaret, K.S. Liver organogenesis promoted by endothelial cells prior to vascular function. *Science* 294, 559-563 (2001).

Schmidt, C. et al. Scatter factor/hepatocyte growth factor is essential for liver development. *Nature* 373, 699-702 (1995).

(Continued)

*Primary Examiner* — Emily A Cordas
*Assistant Examiner* — Briana N Ebbinghaus
(74) *Attorney, Agent, or Firm* — Casimir Jones, S.C.; J. Mitchell Jones

(57) ABSTRACT

The present invention relates to in vitro methods for production of liver organoids.

20 Claims, 1 Drawing Sheet

(56) References Cited

OTHER PUBLICATIONS

Apte, U. et al. Activation of Wnt/beta-catenin pathway during hepatocyte growth factor-induced hepatomegaly in mice. *Hepatology* 44, 992-1002 (2006).
Xie, B. et al. A two-step lineage reprogramming strategy to generate functionally competent human hepatocytes from fibroblasts. *Cell Res* 29, 696-710 (2019).
Koui, Y. et al. An In Vitro Human Liver Model by iPSC-Derived Parenchymal and Non-parenchymal Cells. *Stem Cell Reports* 9, 490-498 (2017).
Oikawa, T. et al. Model of fibrolamellar hepatocellular carcinomas reveals striking enrichment in cancer stem cells. *Nat Commun* 6, 8070, 17 pages (2015).
Martin-Mateos, R. et al. Enhancer of Zeste Homologue 2 Inhibition Attenuates TGF-ß Dependent Hepatic Stellate Cell Activation and Liver Fibrosis. *Cell Mol Gastroenterol Hepatol* 7, 197-209 (2019).
Marcu, R. et al. Human Organ-Specific Endothelial Cell Heterogeneity. *iScience* 4, 20-35 (2018).
Cheng, H.C., Yang, C.M. & Shiao, M.S. Zonation of cholesterol and glycerolipid synthesis in regenerating rat livers. *Hepatology* (Baltimore, Md.) 17, 280-286 (1993).
Ben-Moshe, S. & Itzkovitz, S. Spatial heterogeneity in the mammalian liver. *Nat Rev Gastroenterol Hepatol* 16, 395-410 (2019).
Brosch, M. et al. Epigenomic map of human liver reveals principles of zonated morphogenic and metabolic control. *Nat Commun* 9, 11 pages, 4150 (2018).
Moorman, A.F., Vermeulen, J.L., Charles, R. & Lamers, W.H. Localization of ammonia-metabolizing enzymes in human liver: ontogenesis of heterogeneity. *Hepatology* 9, 367-372 (1989).
Bissell, D.M., Wang, S.S., Jarnagin, W.R. & Roll, F.J. Cell-specific expression of transforming growth factor-beta in rat liver. Evidence for autocrine regulation of hepatocyte proliferation. *J Clin Invest* 96, 447-455 (1995).
Samarasinghe, D.A., Tapner, M. & Farrell, G.C. Role of oxidative stress in hypoxia-reoxygenation injury to cultured rat hepatic sinusoidal endothelial cells. *Hepatology* 31, 160-165 (2000).
Liang, Y. et al. Temporal Analyses of Postnatal Liver Development and Maturation by Single Cell Transcriptomics. *bioRxiv*, 37 pages, 2021.2007.2014.451852 (2021).
Jensen, K.J., Alpini, G. & Glaser, S. Hepatic Nervous System and Neurobiology of the Liver. *Comprehensive Physiology*, 655-665 (2013).
Rosenquist, G.C. Epiblast origin and early migration of neural crest cells in the chick embryo. *Developmental Biology* 87, 201-211 (1981).
Prasad, M.S. et al. Blastula stage specification of avian neural crest. *Developmental Biology* 458, 64-74 (2020).
Ouchi, R. et al. Modeling Steatohepatitis in Humans with Pluripotent Stem Cell-Derived Organoids. *Cell Metab* 30, 374-384.e376 (2019).
Aizarani, N. et al. A human liver cell atlas reveals heterogeneity and epithelial progenitors. *Nature* 572, 199-204 (2019).
Poyck, P.P.C. et al. Expression of Glutamine Synthetase and Carbamoylphosphate Synthetase I in a Bioartificial Liver: Markers for the Development of Zonation in vitro. *Cells Tissues Organs* 188, 259-269 (2008).
Baxter, M. et al. Phenotypic and functional analyses show stem cell-derived hepatocyte-like cells better mimic fetal rather than adult hepatocytes. *J Hepatol* 62, 581-589 (2015).
Peters, D.T. et al. Asialoglycoprotein receptor 1 is a specific cell-surface marker for isolating hepatocytes derived from human pluripotent stem cells. *Development* 143, 1475-1481 (2016).
Li, Y., Fanning, A.S., Anderson, J.M. & Lavie, A. Structure of the conserved cytoplasmic C-terminal domain of occludin: identification of the ZO-1 binding surface. *Journal of molecular biology* 352, 151-164 (2005).
Orbán, E. et al. Different expression of occludin and ZO-1 in primary and metastatic liver tumors. *Pathol Oncol Res* 14, 299-306 (2008).
Desmet, V.J., van Eyken, P. & Sciot, R. Cytokeratins for probing cell lineage relationships in developing liver. *Hepatology* 12, 1249-1251 (1990).
Kasprzak, A. & Adamek, A. Mucins: the Old, the New and the Promising Factors in Hepatobiliary Carcinogenesis. *Int J Mol Sci* 20 30 pages (2019).
Wimmer, R.A. et al. Human blood vessel organoids as a model of diabetic vasculopathy. *Nature* 565, 505-510 (2019).
Strauss, O., Phillips, A., Ruggiero, K., Bartlett, A. & Dunbar, P.R. Immunofluorescence identifies distinct subsets of endothelial cells in the human liver. *Sci Rep* 7, 44356, 13 pages (2017).
Sorensen, Kristine, S.K., Simon-Santamaria, J., McCuskey, R.S. & Smedsrød, B. Liver Sinusoidal Endothelial Cells, Comprehensive Physiology, vol. 5., 1751-1774 (2015).
Ginhoux, F. & Jung, S. Monocytes and macrophages: developmental pathways and tissue homeostasis. *Nat Rev Immunol* 14, 392-404 (2014).
Hoeffel, G. et al. C-Myb(+) erythro-myeloid progenitor-derived fetal monocytes give rise to adult tissue-resident macrophages. *Immunity* 42, 665-678 (2015).
Beljaars, L. et al. Hepatic Localization of Macrophage Phenotypes during Fibrogenesis and Resolution of Fibrosis in Mice and Humans. *Front Immunol* 5, 430, 11 pages (2014).
Wilson, N.K. et al. Combinatorial Transcriptional Control In Blood Stem/Progenitor Cells: Genome-wide Analysis of Ten Major Transcriptional Regulators. *Cell Stem Cell* 7, 532-544 (2010).
Geerts, A. On the origin of stellate cells: mesodermal, endodermal or neuro-ectodermal? *Journal of Hepatology* 40, 331-334 (2004).
Ogu, C.C. & Maxa, J.L. Drug interactions due to cytochrome P450. *Proc* (*Bayl Univ Med Cent*) 13, 421-423 (2000).
Cerny, M.A. Prevalence of Non-Cytochrome P450-Mediated Metabolism in Food and Drug Administration-Approved Oral and Intravenous Drugs: 2006-2015. *Drug Metabolism and Disposition* 44, 1246-1252 (2016).
Wang, D. et al. Human carboxylesterases: a comprehensive review. *Acta Pharm Sin B* 8, 699-712 (2018).
Cui, Y., König, J., Leier, I., Buchholz, U. & Keppler, D. Hepatic Uptake of Bilirubin and Its Conjugates by the Human Organic Anion Transporter SLC21A6. *Journal of Biological Chemistry* 276, 9626-9630 (2001).
Dhar, A. et al. Thrombin and factor Xa link the coagulation system with liver fibrosis. *BMC Gastroenterology* 18, 60, 9 pages (2018).
Hollestelle, M.J. et al. Tissue distribution of factor VIII gene expression in vivo—a closer look. *Thromb Haemost* 86, 855-861 (2001).
Pandey, E., Nour, A.S. & Harris, E.N. Prominent Receptors of Liver Sinusoidal Endothelial Cells in Liver Homeostasis and Disease. *Frontiers in Physiology* 11, 21 pages (2020).
Dhawan, A., Mitry, R.R. & Hughes, R.D. Hepatocyte transplantation for liver-based metabolic disorders. *Journal of inherited metabolic disease* 29, 431-435 (2006).
Halloin, C. et al. Continuous WNT Control Enables Advanced hPSC Cardiac Processing and Prognostic Surface Marker Identification in Chemically Defined Suspension Culture. *Stem Cell Reports* 13, 775, 366-379, (2019).
Ackermann, M. et al. Bioreactor-based mass production of human iPSC-derived macrophages enables immunotherapies against bacterial airway infections. *Nat Commun* 9, 5088, 13 pages (2018).
Wendon, J. et al. EASL Clinical Practical Guidelines on the management of acute (fulminant) liver failure. *Journal of Hepatology* 66, 1047-1081 (2017).
Bernal, W. et al. Outcome after wait-listing for emergency liver transplantation in acute liver failure: A single centre experience. *Journal of Hepatology* 50, 306-313 (2009).
Germani, G. et al. Liver transplantation for acute liver failure in Europe: Outcomes over 20 years from the ELTR database. *Journal of Hepatology* 57, 288-296 (2012).
Siller, R. et al. Development of a rapid screen for the endodermal differentiation potential of human pluripotent stem cell lines. *Sci Rep* 6, 37178 (2016).
Siller, R. & Sullivan, G.J. Rapid Screening of the Endodermal Differentiation Potential of Human Pluripotent Stem Cells. *Current Protocols in Stem Cell Biology* 43, 1G.7.1-1G.7.23 (2017).

(56) References Cited

OTHER PUBLICATIONS

Kempf, H. et al. Bulk cell density and Wnt/TGFbeta signalling regulate mesendodermal patterning of human pluripotent stem cells. *Nature Communications* 7, 13602 (2016).
Lunova, M. et al. Light-induced modulation of the mitochondrial respiratory chain activity: possibilities and limitations. *Cell Mol Life Sci* 77, 2815-2838 (2020).
De Chaumont, F et al. Icy: an open bioimage informatics platform for extended reproducible research. *Nat Methods* 9, 690-696 (2012).
Karinen, R. et al. Determination of heroin and its main metabolites in small sample vols. of whole blood and brain tissue by reversed-phase liquid chromatography-tandem mass spectrometry. *J Anal Toxicol* 33, 345-350 (2009).
Falcon, S. & Gentleman, R. Using GOstats to test gene lists for GO term association. *Bioinformatics* 23, 257-258 (2007).
Xiang, Y. et al. hESC-Derived Thalamic Organoids Form Reciprocal Projections When Fused with Cortical Organoids. *Cell Stem Cell* 24, 487-497.e487 (2019).
Butler, A., Hoffman, P., Smibert, P., Papalexi, E. & Satija, R. Integrating single-cell transcriptomic data across different conditions, technologies, and species. *Nat Biotechnol* 36, 411-420 (2018).
Cakir, B. et al. Engineering of human brain organoids with a functional vascular-like system. *Nat Methods* 16, 1169-1175 (2019).
Subramanian, A. et al. Gene set enrichment analysis: a knowledge-based approach for interpreting genome-wide expression profiles. *Proc Natl Acad Sci U S A* 102, 15545-15550 (2005).
Trapnell, C., Pachter, L. & Salzberg, S.L. TopHat: discovering splice junctions with RNA-Seq. *Bioinformatics* 25, 1105-1111 (2009).
Anders, S., Pyl, P.T. & Huber, W. HTSeq—a Python framework to work with high-throughput sequencing data. *Bioinformatics* 31, 166-169 (2015).
Risso, D., Ngai, J., Speed, T.P. & Dudoit, S. Normalization of RNA-seq data using factor analysis of control genes or samples. *Nat Biotechnol* 32, 896-902 (2014).
Zhu, F. et al. A modified method for implantation of pluripotent stem cells under the rodent kidney capsule. *Stem Cells Dev* 23, 2119-2125 (2014).
Shultz, L.D. et al. Subcapsular transplantation of tissue in the kidney. *Cold Spring Harb Protoc* 2014, 737-740 (2014).

* cited by examiner

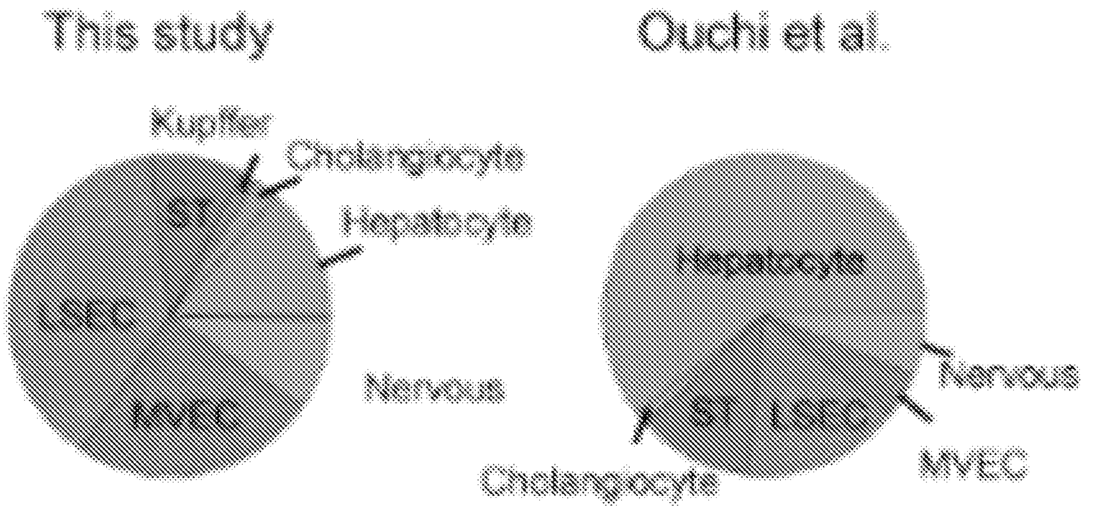
FIG. 2
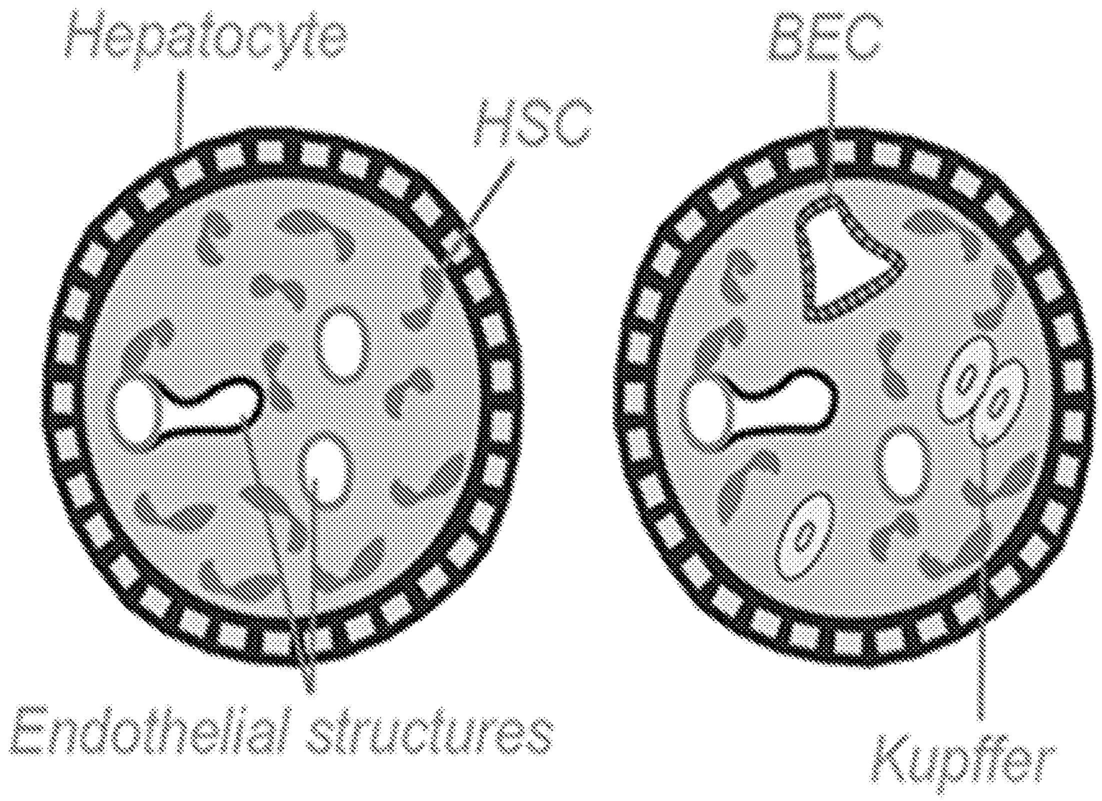

ARTIFICAL LIVER ORGANOIDS AND METHODS OF THEIR PRODUCTION

FIELD OF THE INVENTION

The present invention relates to in vitro methods for production of liver organoids.

BACKGROUND OF THE INVENTION

Prior art approaches for culturing and differentiating hepatocytes suffer a number of drawbacks, including a reliance on extracellular matrices and costly growth factors in purified form. Furthermore, the methods perform poorly with respect to obtaining diversity, structure and organization of the hepatocytes.

Ouchi, R. et al., Modeling Steatohepatitis in Humans with Pluripotent Stem Cell-Derived Organoids, Cell Metab 30, 374-384.e376 (2019) describes a process for making liver organoids. The method is cumbersome and involves manual transfer into Matrigel™ matrix drops and the use of expensive growth factor reagents including Hepatocyte Growth Factor (HGF).

What is needed in the art are methods for the development of liver organoids in culture that are scalable, and which may use small molecule reagents.

SUMMARY OF THE INVENTION

The present invention relates to methods for in vitro production of liver organoids. The method is suitable for large scale production of vascularized liver organoids comprising differentiated hepatocytes. The method is suitable for upscaling and can be performed based on supplementing culture media with small molecules only. Accordingly, neither extracellular matrices (ECM) or expensive protein growth factors are needed. It was found that cell density in the first step affected the cell composition of the obtained liver organoids. In particular, the claimed method allows reduction of the fraction of organoids comprising undesirable cardiomyocytes. The organoids obtained by the claimed method also displayed increased secretion of alpha 1 antitrypsin. Thus, the present disclosure provides methods and products that may serve as an inexpensive approach to produce massive quantities of liver organoids with enhanced function and maturity, which may be useful for a variety of applications from cellular therapy, tissue engineering, drug toxicity assessment, disease modelling, and basic developmental research.

In some preferred embodiments, the present invention provides in vitro methods for production of liver organoids comprising: a. suspending vertebrate pluripotent stem cells in a liquid base medium at a density of from 0.5 to 5.0 ml medium per one million pluripotent stem cells; b. incubating the suspended pluripotent stem cells under agitation so that the pluripotent stem cells form aggregates; c. incubating the aggregates from step b. in the presence of a WNT agonist; d. incubating the aggregates from step c. in medium without WNT agonist; e. incubating the aggregates from step d. in the presence of DMSO; and f. incubating the aggregates from step e. in the presence of a glucocorticoid and an agonist of the hepatocyte growth factor receptor (HGFR) for from 10 to 200 days.

In other preferred embodiments, the present invention provides in vitro methods for production of liver organoids comprising: a. suspending vertebrate pluripotent stem cells in a liquid base medium at a density of from 0.5 to 5.0 ml medium per one million pluripotent stem cells; b. incubating the suspended pluripotent stem cells for 12 to 30 hours under agitation so that the pluripotent stem cells form aggregates; c. incubating the aggregates from step b. in the presence of a WNT agonist for 12 to 30 hours; d. incubating the aggregates from step c. in medium without WNT agonist for 12 to 30 hours; e. incubating the aggregates from step d. in the presence of DMSO for 4 to 9 days; and f. incubating the aggregates from step e. in the presence of a glucocorticoid and an agonist of the hepatocyte growth factor receptor (HGFR) for from 10 to 200 days.

In some preferred embodiments, the liquid base medium in step a. comprises an inhibitor of ROCK-I and/or ROCK-II. In some preferred embodiments, the vertebrate cells are mammalian cells or human cells. In some preferred embodiments, the incubation is performed in humidified air comprising 5% $CO_2$ at 37° C. In some preferred embodiments, the incubation in any of steps b., c., d. and e. is performed under orbital shaking of 50 to 100 rounds per minute. In some preferred embodiments, the medium in step c. comprises insulin. In some preferred embodiments, the WNT agonist in step c. is a glycogen synthase kinase (GSK) 3 inhibitor. In some preferred embodiments, the medium in step c. comprises from 2 to 6 μM CHIR99021. In some preferred embodiments, the agonist of the hepatocyte growth factor receptor is N-hexanoic-Tyr, Ile-6 aminohexanoic amide provided at a concentration of 80 to 120 nM. In some preferred embodiments, the glucocorticoid in step f. is dexamethasone provided at a concentration of from 80 to 120 nM.

In some preferred embodiments, the present invention provides an artificial liver organoid comprising hepatocytes, neurons, macrovascular endothelial cells (MVEC), liver sinusoidal endothelial cell (LSEC), hepatic stellate cells, Kupffer cells and cholangiocytes, wherein the artificial liver organoid comprises at least one lumen lined with $CD31^+$ cells.

In some preferred embodiments, artificial liver organoid comprises from 10 to 50% hepatocytes, 5 to 15% neurons, 20 to 40% macrovascular endothelial cells (MVEC), 25 to 50% liver sinusoidal endothelial cells (LSEC), 3 to 40% hepatic stellate cells, 1 to 3% Kupffer cells and 1 to 5% cholangiocytes, which together add up to 100%.

In some preferred embodiments, the organoids described above (as well as those produced by the described methods) express one or more of ALB, A1AT, and ASGPR1. In some preferred embodiments, the organoids express one or more of APOA2, TDO2 and TTR. In some preferred embodiments, the organoids CYP3A4 and/or CYP3A7. In some preferred embodiments, the organoids one or more of the cell surface markers MARCO, CD45, CD163, CD16A, LY86 and CD86. In some preferred embodiments, the organoids express one or more of the complement components C1QA, C1QB and C1QC. In some preferred embodiments, the organoids express one or more of the macrophage regulators VSIG4 TREM2 and PU.1. In some preferred embodiments, the organoids express the protein(s) CYP2A6 and/or ASGP1. In some preferred embodiments, the organoids express one or more of BGN, CTGF, TPM2, SPARC, IGFBP, TAGLN, DCN, CCL2, and COL1A1. In some preferred embodiments, the organoids express the protein(s) CYP1A2 and/or CYP3A4. In some preferred embodiments, the protein(s) CYP1A2 and/or CYP3A4 are expressed in amount sufficient to metabolism caffeine and/or acetaminophen. In some preferred embodiments, the organoids express carboxyl esterases. In some preferred embodiments, the carboxyl esterases are expressed in an amount sufficient to metabolize heroin. In some preferred embodiments, the organoids are able to uptake unconjugated bilirubin. In some preferred embodiments, the organoids express one or more of the coagulation factors F7, F8, F10, FBG and anti-thrombin (AT).

In some preferred embodiments, the present invention provides a suspension comprising artificial liver organoids as described above.

In some preferred embodiments, the present invention provides a kit comprising multiple vessels, wherein at least one vessel contains an inhibitor of ROCK-I and/or ROCK-II, wherein at least one vessel contains a WNT agonist, wherein at least one vessel contains a glucocorticoid, wherein at least one vessel contains an agonist of the hepatocyte growth factor receptor (HGFR), and instructions for performing a method as described above. In particular, the active ingredients in the vessels may comprise non-protein small molecules only.

In some preferred embodiments, the present invention provides methods comprising providing an artificial liver organoid as described above or made by a method as described above, contacting the artificial liver organoid with a test reagent; and assaying the effect of the test reagent on the artificial liver organoid.

In some preferred embodiments, the present invention provides methods comprising providing an artificial liver organoid as described above or made by a method as described above, and transplanting the artificial liver organoid into a subject.

BRIEF DESCRIPTION OF THE FIGURES

FIG. 1 provides pie charts comparing the cellular composition of liver organoids of the present invention in comparison to those of Ouchi et al.

FIG. 2 provides schematic cross-sections of liver organoids of the instant invention.

DETAILED DESCRIPTION OF THE INVENTION

The in vitro method herein can be performed based on small molecules rather than expensive growth factor proteins, and it mimics in vivo liver development. The methods described herein (and the artificial liver organoids resulting from the methods) address the technical problem of providing artificial liver organoids that have the same gene expression, protein expression and functional attributes of in vivo liver cells and organs. The extensive characterization of the artificial liver organoids and benchmarking against liver tissue and cells presented in the Experimental section demonstrates that the artificial liver organoids of the present invention recapitulate liver function in vitro and in manner not observed in other prior art protocols for differentiation of stem cells into liver cell lineages.

The initial step involves providing vertebrate pluripotent stem cells in a suitable liquid base medium. As used herein, suitable liquid base medium means any liquid medium containing components that are sufficient for cell growth and/or maintenance of a desired cell type in an in vitro culture system. Typically, the base medium will comprise amino acids, inorganic salts, an energy source such as glucose, serum or a serum substitute and/or growth factors.

Suitable base media are available from a variety of commercial providers. Suitable base media that may be used in the methods of the present invention include, but are not limited to, E8 Medium (ThermoFisher Scientific), RPMI 1640 (Life Technologies), Knockout DMEM (Life Technologies), and the like. It will be understood that different base media may be substituted for the base media exemplified herein as long as the base medium supports the particular stage of culture. RPMI 1640 Medium is unique from other media because it contains the reducing agent glutathione and high concentrations of vitamins. RPMI 1640 Medium contains biotin, vitamin B12, and PABA, which are not found in Eagle's Minimal Essential Medium or Dulbecco's Modified Eagle Medium.

In some preferred embodiments, the vertebrate pluripotent stem cells are human pluripotent stem cells. Human pluripotent stem cell lines (hPSCs) are readily available from commercial providers, so there is no need for destruction of human embryos to obtain the starting materials. The present invention is not limited to the use of any particular hPSC. For example, the human pluripotent stem cell lines utilized in the examples contained herein include the human embryonic stem cell line H1 (WiCell) and the previously described hPSC lines AG27 (reprogrammed using retrovirus from AG05836B fibroblasts, obtained from Coriell Cell Repositories), and Detroit RA (reprogrammed using Sendai virus from Detroit 551 fibroblasts, obtained from ATCC) using known methods. hPSCs were maintained under feeder free conditions on Geltrex (Life Technologies) coated tissue culture plates using E8 medium.

Culturing of many types of pluripotent stem cells requires supplementing the medium with an inhibitor of ROCK-I and/or ROCK-II, however, some stem cell lines are also independent of ROCK-I and/or ROCK-II inhibition. The initial step may thus be performed by seeding cells into a suitable base medium comprising an inhibitor of ROCK-I and/or ROCK-II. However, it may also be performed by adding an inhibitor of ROCK-I and/or ROCK-II to a medium comprising the cells. Suitable ROCK-I and/or ROCK-II inhibitors are well known to skilled persons and include, but are not limited to Fasudil, Y-27632, Y-39983, Wf-536, SLx-2119, Azabenzimidazole-aminofurazans, DE-104, H-1152P, XD-4000, HMN-1152, BA-210, BA-215, BA-285, BA-1037, Ki-23095, and VAS-012.

In some preferred embodiments, the first step (i.e., Step a.) of a method of the present invention comprises seeding pluripotent stem cells in a suitable base culture medium at a density of from 0.5 to 5.0 ml medium/million cells. The medium utilized in Step a. may be referred to as aggregation medium. In some still more preferred embodiments, the pluripotent stem cells are seeded at a density of from 2.0 to 4 ml medium/million cells. In some still more preferred embodiments, the pluripotent stem cells are seeded at a density of from 1.0 to 4.5 ml medium/million cells, 2.0 to 4.0 ml medium/million cells, 3.0 to 4.0 ml medium/million cells, and most preferably 3.5 to 4.0 ml medium/million cells In some preferred embodiments, the medium comprises a ROCK inhibitor. In some still more preferred embodiments, the ROCK inhibitor is Y-27632 (BOC Sciences). In some particularly preferred embodiments, as demonstrated in the Experimental section, human pluripotent stem cells are seeded into 125 ml or 500 ml cell culture Erlenmeyer flasks (Corning) at a bulk cell density of 3.5-4 ml of media/million cells, in E8 supplemented with 10 μM Y-27632 (BOC Sciences).

In some preferred embodiments, a second step (i.e., Step b.) of a method of the instant invention comprises culture of the pluripotent stem cells to provide a suspension comprising cell aggregates. Accordingly, following the initial seeding step, the cells are preferably cultured in suspension (in the aggregation medium) under conditions that allow formation of cell aggregates. In some preferred embodiments, the culturing is performed in a suitable liquid medium under agitation preventing the cells from adhering to the substrate. In some still more preferred embodiments, the cells are incubated for 12 to 30 hours under agitation allowing aggregation of cells, but still avoiding adherence to the substrate. In some particularly preferred embodiments, as demonstrated in the Experimental section, the cells were allowed to self-organise into aggregates for 24 hours on an orbital shaker at 70 RPM in a humidified 37° C., 5% $CO_2$ incubator. In some particularly preferred embodiments, the aggregates in Step b. are characterized as comprising maintaining pluripotency markers (i.e., OCT4, SOX2 and NANOG) over 24 hours.

In some preferred embodiments, a third step (i.e., Step c.) of a method of the present invention comprises treatment of the aggregates to drive the aggregates from pluripotency to primitive streak/mesendoderm (e.g., after 1 day in culture) and then towards definitive endoderm (e.g., after 2 days in culture). Accordingly, in some preferred embodiments, the aggregates from Step b. are preferably contacted with a WNT agonist provided in a suitable base culture medium. The medium utilized in Step c. may be referred to as WNT medium. In some preferred embodiments, the aggregates are collected from the suspension culture by centrifugation and resuspended in a suitable base medium supplemented with a WNT agonist. Suitable WNT agonists are known in the art. In some preferred embodiments, the WNT agonist is a glycogen synthase kinase 3 (GSK-3) inhibitor. In some particularly preferred embodiments, the WNT agonist is CHIR99021 or BIO. In some particularly preferred embodiments, the aggregates are cultured in the presence of the WNT agonist for from about 12 to 30 hours, and most preferably for about 24 hours. In preferred embodiments, the culture is a suspension culture in a suitable liquid medium under agitation to prevent the aggregates from adhering to the substrate and from disintegration into single cells. For example, the aggregates may be incubated for 12 to 30 hours under gentle agitation, for example in an orbital shaker at 70 RPM in a humidified 37° C., 5% $CO_2$ incubator. In some particularly preferred embodiments, as demonstrated in the Experimental section, the aggregates from Step b. are suspended at a density of 3.5 ml/million cells in RPMI 1640 (Life Technologies) supplemented with B-27 with insulin and 3 or 4 μM CHIR99021 (BOC Sciences) and cultured for 24 hours.

In some preferred embodiments, a fourth step (i.e., Step d.) of a method of the present invention comprises culture of the aggregates from Step c. in a base medium that does not comprise a WNT agonist. The medium utilized in Step c. may be referred to as WNT-free medium. Accordingly, in some preferred embodiments, the WNT-treated aggregates are washed to remove the WNT agonist and then cultured in suspension. In some particularly preferred embodiments, the aggregates from Step c. are collected by centrifugation and resuspended in a base medium without a WNT agonist. In some particularly preferred embodiments, the aggregates are then cultured in the medium without WNT agonist for about 12 to 30 hours, and most preferably for about 24 hours. Suitable culture conditions comprise gentle agitation, for example in an orbital shaker at 70 RPM in a humidified 37° C., 5% $CO_2$ incubator as described in the Experimental section. In some particularly preferred embodiments, aggregates resulting from Steps c. and d. are characterized in exhibiting one or more markers of both mesoderm and definitive endoderm (DE): T, GSC, FOXA2, SOX17, HHEX and CER1.

In some preferred embodiments, a fifth step (i.e., Step e.) of a method of the present invention comprises treatment of the aggregates to drive differentiation into hepatic endoderm. The medium utilized in Step e. may be referred to as hepatic endoderm medium. Accordingly, in some preferred embodiments, the aggregates from Step d. are collected and transferred to a suitable base medium supplemented with DMSO. In some preferred embodiments, the aggregates are collected from the suspension culture by centrifugation and resuspended in a suitable base medium supplemented with DMSO. In some particularly preferred embodiments, as described in the Experimental section, the aggregates are suspended in a suitable base medium comprising DMSO and incubated, preferably for about 4 to 9 days, under gentle agitation. For example, as demonstrated in the Experimental section, the aggregates are collected and resuspended at from 1.5 to 4 ml/million cells (e.g., 3.5 ml/million cells (input number of cells)) in Knockout DMEM (Life Technologies), 20% (vol/vol) Knockout Serum Replacement (Life Technologies), 1% dimethyl sulfoxide (Sigma-Aldrich), non-essential amino acids (NEAA—Life Technologies), 2-mercaptoethanol (Life Technologies) and Glutamax (Life Technologies) and incubated for 5 days, with medium changes every 48 hours. In some particularly preferred embodiments, aggregates resulting from Step e. are characterized in exhibiting one or more hepatic markers (e.g., AFP, CEBPa, HNF4a, TBX3 and/or TTR) and by a decrease in expression of DE markers such as HHEX SOX17 and/or GATA4. In some preferred embodiments, the outer epithelial layer of cells of the aggregates express ECAD (CDH1), FOXA2, and CK8, as well as being HNF4-alpha and AFP positive.

In some preferred embodiments, a sixth step (i.e., Step f.) of a method of the present invention comprises treating the aggregates under conditions such that the aggregates mature into liver organoids. The medium utilized in Step f. may be referred to as liver organoid maturation medium. Accordingly, in some preferred embodiments, the aggregates are collected from the suspension culture by centrifugation and resuspended in a suitable base medium supplemented with one or more factors that drive maturation of hepatic endoderm into mature liver tissue. In some preferred embodiments, the one or more factors that drive maturation of hepatic endoderm into mature liver tissue include, but are not limited to, a glucocorticoid and an agonist of the hepatocyte growth factor receptor (HGFR). Suitable glucocorticoids include, but are not limited to, dexamethasone, cortisol, hydrocortisone and prednisolone. Suitable hepatic growth factor receptor agonists include, but are not limited to, N-hexanoic-Tyr, Ile-6 aminohexanoic amide (dihexa), HGF (hepatic growth factor) and other HGF agonists. In some preferred embodiments, the aggregates are then cultured under conditions that allow development into liver organoids. In some preferred embodiments, the aggregates are cultured for from about 10 to 200 days under gentle agitation. For example, as demonstrated in the Experimental section, in some particularly preferred embodiments the aggregates are cultured in a medium comprising Lebovitz L-15 base medium supplemented with 8.3% foetal bovine serum (FBS—Biowest), 8.3% Tryptose Phosphate Broth (Sigma-Aldrich), Hydrocortisone (Sigma-Aldrich), Ascorbic Acid (Sigma-Aldrich), Glutamax (Life Technologies), 100 nM Dexamethasone (Sigma-Aldrich), and 100 nM N-hexanoic-Tyr, Ile-6 aminohexanoic amide (dihexa) (Active Peptide). The resulting organoids may, for example, be cultured from 10 to 200 days, from 10 to 100 days, from 10 to 75 days, from 10 to 50 days, or from 10 to 20 days, etc., with a medium exchange at suitable intervals (e.g., about every 48 hours) during maturation into liver organoids. In some preferred embodiments, liver organoids resulting from Step f. are characterized in exhibiting one or more markers of hepatic maturation and tissue like complexity including, but not limited to ALB, A1AT, ASGPR1, APOA2, TDO2, TTR, P450 (CYP) 2A6, 3A4 and CYP3A7 and combinations thereof.

In the description above, reference is made to various markers at different stages of the culture process. Markers may be assayed by any suitable method including, but not limited to immunofluorescence, FACS, PCR, qPCR, RT-qPCR, scRNAseq and related methods as are known in the art.

Cultures according to the described processes comprise a significant fraction of liver organoids which may be maintained over weeks and months. The liver organoids obtained by the methods of the instant invention are characterized as comprising parenchymal and non-parenchymal cell types of the liver and by the presence of detectable vascular structures. The organoids exhibit liver functions including drug metabolism, production of serum proteins, including the coagulation factors, bilirubin uptake and urea synthesis. The organoids can be transplanted into mice maintaining production of human albumin long term.

As used herein, liver organoids, means organotypic-like structures comprising cells typical of the liver. In some preferred embodiments, the liver organoids have a diameter of from about 50 to about 1 mm. In some preferred embodiments, the liver organoids of the present invention comprise hepatocytes, liver sinusoidal endothelial cells (LSEC), macrovascular endothelial cells (MVEC), peripheral nervous system-like cells, Kupffer cells, cholangiocytes and hepatic stellate cells (HSC (also designated as ST cells in FIG. 1)). The distribution of these cell types in the liver organoids of the present invention is provided in FIG. 1 in comparison to the organoids of Ouchi et al. As can be seen, the organoids of the present invention can be characterized in containing more LSEC than hepatocytes, more MVEC than hepatocytes, more than 50% total LSEC and MVEC combined, and a significant presence of Kupffer cells. FIG. 2 provides schematic cross sections of liver organoids of the present invention. As can be seen, the liver organoids are characterized in comprising an outer hepatocyte layer, vascular endothelial structures, hepatic stellate cells (HSC), Kupffer cell structures and biliary epithelial cells (BEC) structures. In some preferred embodiments, cells expressing the cell surface marker (MARCO, CD45, CD163, CD16A, LY86 and CD86), complement components (C1QA, C1QB and C1QC) and macrophage regulators (VSIG4, TREM2 and PU.1) are enriched in liver organoids produced as described herein.

The clinically approved molecular adsorbents recirculating system (MARS) from Gambro and the fractionated plasma separation and adsorption (FPSA) from Prometheus are able to take over the liver detoxification functions ex vivo while a patient's liver recovers through regeneration. The organoids described herein, may thus have utility in artificial liver devices which essentially comprise a bioreactor to be connected to a patient circulation system. When such devices meet all requirements for the manufacture of advanced therapy medicinal products, they can be used in clinical trials. Accordingly, the present disclosure also provides an ex vivo method of preventing diseases caused by liver failure, e.g. hepatic encephalopathy, comprising the step of culturing the organoids disclosed herein in an artificial liver device approved for clinical use. In such devices, the liver organoids would be separated from the blood stream by a membrane allowing passage of nutrients and toxins but preventing the liver organoids from passing. Because the liver organoids are much larger than single hepatocytes, the membrane can be much more porous than in conventional artificial liver devices. This may allow improved flow resistance.

In some preferred embodiments, methods, reagents, and kits described herein, as well as the artificial liver organoids generated therewith, find use in various research, diagnostic, clinical, and therapeutic applications. In some embodiments, artificial liver organoids are used for direct transplantation into a subject. In some embodiments, artificial liver organoids generated by methods herein are useful for diagnostic, prognostic, and/or therapeutic uses.

In some embodiments, the isolated liver organoids may be directly transplanted in a subject. If appropriate, cells are co-administered with one or more pharmaceutical agents or bioactives that facilitate the survival and function of the transplanted cells. These agents may include, for example, insulin, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-I) and II, GLP-1 and GLP-2 mimetibody, Exendin-4, retinoic acid, parathyroid hormone, MAPK inhibitors, etc.

Cells generated with methods and reagents herein may be implanted as dispersed cells or formed into implantable clusters. In some embodiments, cells are provided in biocompatible degradable polymeric supports; porous, permeable, or semi-permeable non-degradable devices; or encapsulated (e.g., to protect implanted cells from host immune response, etc.). Cells may be implanted into an appropriate site in a recipient. Suitable implantation sites may include, for example, a liver or kidney of a subject.

In further embodiments, artificial liver organoids may be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al, eds.); and Methods of Immunological Analysis (Masseyeff et al, eds., Weinheim: VCH Verlags GmbH). General techniques involved in preparation of mR A and cDNA libraries are described in R A Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). Relatively homogeneous cell populations are particularly suited for use in drug screening and therapeutic applications.

In some embodiments, the artificial liver organoids generated by methods provided herein are used to screen for agents (e.g., small molecule drugs, peptides, polynucleotides, and the like) or environmental conditions (such as culture conditions or manipulation) that affect the organoids. Particular screening applications relate to the testing of pharmaceutical compounds in drug research. Assessment of the activity of candidate pharmaceutical compounds generally involves combining the cells with the candidate compound, determining any change in the morphology, marker phenotype, or metabolic activity of the organoid that is attributable to the compound (compared with untreated cells or cells treated with an inert compound), and then correlating the effect of the compound with the observed change. Any suitable assays for detecting changes associated with test agents may find use in such embodiments. The screening may be done, for example, either because the compound is designed to have a pharmacological effect on liver cell types or organoids, because a compound designed to have effects elsewhere may have unintended side effects, or because the compound is part of a library screen for a desired effect. Two or more drugs can be tested in combination (by combining with the cells either simultaneously or sequentially), to detect possible drug-drug interaction effects. In some applications, compounds are screened for cytotoxicity.

In some embodiments, methods and systems are provided for assessing the safety and efficacy of drugs that act upon liver cells or the organ as a whole, or drugs that might be used for another purpose but may have unintended effects upon liver cells of the organ as a whole. In some embodiments, cells described herein find use in high throughput screening (HTS) applications. In some embodiments, a HTS screening platform is provided (e.g., cells and plates) that allows for the rapid testing of large number (e.g., $1\times10^3$, $1\times10^4$, $1\times10^5$, $1\times10^6$ or more) of agents (e.g., small molecule compounds, peptides, etc.). In some embodiments, artificial liver organoids generated using methods and reagents described herein are utilized for therapeutic delivery to a subject. Cells may be placed directly in contact with subject tissue or may be otherwise sealed or encapsulated (e.g., to avoid direct contact). In embodiments in which cells are encapsulated, exchange of nutrients, gases, etc. between the encapsulated cells and the subject tissue is allowed. In some embodiments, cells are implanted/transplanted on a matrix or other delivery platform.

EXPERIMENTAL

Generation of Liver Organoids In Vitro

The liver is the largest endocrine organ in the body and is critical for maintaining homeostasis, serving as the primary site of xenobiotic metabolism, production of coagulation factors, and removal of ammonia as well as a multitude of other essential functions[1]. In the setting of liver failure, no other curative treatment approach besides liver transplantation (LTX) exists. Additionally, the gold standard for the evaluation of hepatic metabolism and drug toxicity, amongst other things, are primary human hepatocytes (PHHs). However, these are limited in supply and rapidly lose function in vitro. This highlights the necessity to identify potential surrogates to fill this void.

Human pluripotent stem cells (hPSCs) have the ability to self-organise into organotypic structures called organoids. However, organoid models do not fully recapitulate the cellular diversity and architectural features of the organ in question[2]. The lack of such organotypic in vitro models has led us to develop an approach that utilises a suspension culture system that leverages off the ability of hPSCs to self-aggregate on seeding as single cells. In addition, we have overcome the requirement to pattern the hPSCs in a 2D format to definitive endoderm (See Ouchi et al 2019) by directly patterning the 3D pluripotent aggregates through the addition of small molecules (growth factor mimetics), in an extracellular matrix (ECM) independent manner that is scalable to generate "mini-liver" organoids which contain vasculature while recapitulating the complexity of cell types associated with the liver.

Materials and Methods hPSC Culture

The human pluripotent stem cell lines utilised in this study were as follows: the human embryonic stem cell line H1 (WiCell) and the previously described hiPSC lines AG27 (reprogrammed using retrovirus from AG05836B fibroblasts, obtained from Coriell Cell Repositories), and Detroit RA (reprogrammed using Sendai virus from Detroit 551 fibroblasts, obtained from ATCC)[4,5,57,58]. hPSCs were maintained under feeder free conditions on Geltrex (Life Technologies) coated tissue culture plates using Essential 8 medium made in house as described previously[58].

Culture of Primary Human Hepatocytes

Human plateable hepatocytes (primary hepatocytes (PH)) were purchased from Thermo Fisher Scientific and cultured in Williams' Medium E (1×, no phenol red) (Thermo Fisher Scientific) following the manufacturer's instructions.

2D Hepatocyte-Like-Cell Differentiation

Cells were differentiated to hepatocyte-like-cells (HLCs) in 2D as described previously[4,8,58]. Briefly, cells were initially seeded onto Geltrex coated tissue culture plates as single cells after incubation with Accutase (Life Technologies). Optimal seeding density was previously established empirically as described in Mathapati et al., 20164. Differentiation to HLCs was through a 3 stage process consisting of differentiation to definitive endoderm (DE—Phase I), hepatic specification to hepatoblasts/hepatic endoderm (HE—Phase II), and finally maturation to hepatocyte like cells (HLCs—Phase III). In order to ensure high-quality 2D differentiation we utilised our recently reported method for lifting and replating hepatic endoderm cells 58. For a detailed protocol of the differentiation process, please see Mathapati et al., 2016 and Siller et al.[58].

Suspension Culture and Differentiation to Liver Organoids

To differentiate hPSCs to organoids the cells were harvested by incubating with Accutase (Life Technologies) for 10 minutes at 37° C. until all cells had detached. The cells were pelleted by centrifugation at 300×g for 5 minutes at room temperature. After counting, the cells were seeded into 125 ml or 500 ml cell culture Erlenmeyer flasks (Corning) at a bulk cell density of 3.5-4 ml of media/million cells, (see 59) in Essential 8 supplemented with 10 μM Y-27632 (BOC Sciences). The cells were allowed to self-organise into aggregates for 24 hours on an orbital shaker at 70 RPM in a humidified 37° C., 5% $CO_2$ incubator. The conditions for suspension culture (orbital shaker at 70 RPM in a humidified 37° C., 5% $CO_2$ incubator) were utilised for all further steps of the differentiation. After aggregate formation, differentiation was commenced to drive pluripotent hPSC aggregates to primitive streak/mesendoderm (day 1) and further patterned towards definitive endoderm (day 2). To initiate differentiation, the hPSC aggregates were collected from the flask and transferred to a 50 ml conical tube and pelleted by centrifugation for 5 minutes at 300×g at room temperature. After removal of the supernatant, the aggregates were resuspended in 3.5 ml/million cells of differentiation medium comprised of RPMI 1640 (Life Technologies) supplemented with B-27 either with or without Insulin (RPMI/B-27+/−) (Life Technologies) depending on the cell line and 3 or 4 μM CHIR99021 (BOC Sciences). Optimal conditions need to be established for each line based on our previously established protocol[4,5,57,58]. The aggregates were then transferred back to the Erlenmeyer flask and incubated for another 24 hours. After 24 hours, the aggregates collected as previously described and the cell pellet was gently resuspended in the same volume of RPMI/B-27+/−, without any small molecules, and transferred back to the Erlenmeyer flask. The aggregates were incubated for a further 24 hours. On day 2 of the differentiation the cells were directed towards hepatic endoderm (day 7). The aggregates were collected as above and resuspended at 3.5 ml/million cells in Knockout DMEM (Life Technologies), 20% (vol/vol) Knockout Serum Replacement (Life Technologies), 1% dimethyl sulfoxide (Sigma-Aldrich), non-essential amino acids (NEAA—Life Technologies), 2-mercaptoethanol (Life Technologies) and Glutamax (Life Technologies) and incubated for 5 days, with medium changes every 48 hours. On day 7, the resulting organoids were switched to medium for maturation to liver organoids. The medium comprised of Lebovitz L-15 base medium supplemented with 8.3% foetal bovine serum (FBS-Biowest), 8.3% Tryptose Phosphate Broth (Sigma-Aldrich), Hydrocortisone (Sigma-Aldrich), Ascorbic Acid (Sigma-Aldrich), Glutamax (Life Technologies), 100 nM Dexamethasone (Sigma-Aldrich), and 100 nM N-hexanoic-Tyr, Ile-6 aminohexanoic amide (dihexa) (Active Peptide). The organoids were cultured from day 7 to day 20, with a medium exchange every 48 hours. Organoids were collected and analysed or maintained in long-term culture as indicated.

Fixation of Organoids

For TEM the organoids were fixed in 1% glutaraldehyde/1% paraformaldehyde (PFA) in 0.12 M phosphate buffer and 0.02 mM $CaCl_2$(pH 7.2-7.5; Sigma) for 4 hours at room temperature, washed in 8% glucose (in 0.12 M phosphate buffer and 0.02 mM CaCl2, pH 7.2-7.5) and post-fixed in 2% $OsO_4$ (in 0.12 M phosphate buffer and 0.02 mM CaCl2, pH 7.4; Sigma) for 90 minutes at room temperature. For histology and immunohistochemical detection the organoids were briefly rinsed in 0.1 M Sorensen buffer (pH 7.4) and immersed in 3% PFA and 0.05% glutaraldehyde in 0.1 M Sorensen buffer (pH 7.4) for 2 hours at room temperature followed by 30 minutes at 4° C. After a thorough washing in 0.1 M Sorensen buffer (pH 7.4), the organoids were dehydrated and embedded in paraffin. 6 μm thick serial sections were cut from paraffin blocks using a microtome and every tenth slide was stained with hematoxylin-eosin for histological examination.

Immunohistochemical detection of cytokeratin 18 and cytokeratin 19 was performed by indirect two-step method in paraffin-embedded sections. After deparaffinization and rehydration of sections, antigen retrieval was performed in HistoStation (Milestone, Sorisole, Italy). Endogenous peroxidase was blocked in 5% H2O2 (3×10 minutes) and then, sections were incubated with primary mouse anti-cytokeratin 18, clone DC10 (DAKO, Glostrup, Denmark; 1:25) or primary mouse anti-cytokeratin 19, clone BA17 (DAKO, Glostrup, Denmark; 1:50) antibody for 1 hour at room temperature. After washing in PBS, the sections were exposed to anti-mouse DAKO EnVision+System-HRP Labeled Polymer (DAKO, Glostrup, Denmark) for 35 minutes at room temperature. Then the reaction was developed with 3,3-diaminobenzidine tetrahydrochloride (Sigma-Aldrich). Sections were dehydrated, counterstained with hematoxylin and mounted in DPX (Sigma-Aldrich). Tissue sections were examined in Olympus BX51 microscope equipped with DP71 camera.

For whole-mount immunofluorescence and confocal imaging organoids were fixed in 4% PFA for 60 minutes, then pelleted (300×g for 5 minutes, low deceleration) and washed in PBS for 20 minutes, repeated three times. Fixed samples were stored in PBS at 4° C. until required. 10 μl of sphere sediment was pipetted onto a coverslip and briefly air-dried followed by centrifugation at 1000×g for 5 minutes. The fixed organoids were blocked for 1 hour in PBS supplemented with 0.1% Triton X-100 (Sigma Aldrich)×100 (PBS-Triton X-100) and 10% goat serum (Life Technologies). The primary antibody was then diluted at the appropriate dilution in PBS-Triton X-100 containing 1% goat serum and incubated overnight at 4° C. The primary antibody was removed and the sample washed for 3×20 minutes in PBS-Triton X-100. All Alexa-Fluor secondary antibodies (Life Technologies) were diluted 1:1500 with PBS-Triton X-100 and added to the samples for 4 hours at 4° C. in the dark and subsequently washed 3 times for 20 minutes in PBS-Triton X-100. To dual label the samples, the above steps (block, primary, secondary) were repeated. Nuclei were counterstained with DRAQ5 at 1:1500 in PBS, for a minimum of 15 minutes before imaging.

Microscopy

Phase-contrast images were obtained using an Axio Primovert upright light microscope (Zeiss). Images were captured using Zen Software (Zeiss). All scale bars represent 100 μm, unless otherwise stated in the figure legends. Confocal images were obtained using an Olympus FV1000 confocal microscope with submersion lenses, images were captured using Olympus Fluoview and compiled using Image J software. Scale bars represent 100 μm unless otherwise stated in the figure legends.

Spinning Disk Confocal Microscopy.

In order to be able to reveal clear organoid visualization we used ultrafast confocal system IXplore SpinSR Olympus (Olympus, Tokyo, Japan). We utilized our previously published imaging settings[60]. The imaging system consists of the following units: an inverted microscope (IX83; Olympus, Tokyo, Japan) and a spinning disc confocal unit (CSUW1-T2S SD; Yokogawa, Musashino, Japan). Fluorescence data for image reconstruction were collected via either a 100× silicone immersion objective (UPLSAPO100XS NA 1.35 WD 0.2 silicone lens, Olympus, Tokyo, Japan) or a 20× objective (LUCPLFLN20XPH NA 0.45 air lens, Olympus, Tokyo, Japan). The following lasers were used to excite fluorophores: 405 nm laser diode (50 mW) and 488 nm laser diode (100 mW). Confocal images were acquired at a 2,048×2,048-pixel resolution. Optical sections were acquired at 1.5-μm and 250-nm intervals along the z-axis for 3D reconstruction of respectively 20× and 100× objectives. The fluorescent images were collected by appropriate emission filters (BA420-460; BA510-550; Olympus, Tokyo, Japan) and captured concurrently by two digital CMOS cameras ORCA-Flash4.0 V3 (Hamamatsu, Hamamatsu City, Japan). Fluorescence confocal images were acquired using software cellSens (Olympus, Tokyo, Japan). Icy open source software was used for image processing and 3D reconstruction[61].

Cryosectioning

PFA fixed organoids were transferred to a cryomold and embedded in OCT compound (Thermo Fisher Scientific) and cooled to −80° C. on a bath of isopropanol on dry ice. The cryo-embedded organoids were then sectioned at 50 μm on a cryotome and transferred to slides. Slides were stored at −80° C. until immunostained and imaged as described above.

Transmission Electron Microscopy

The fixed organoids (described above) were rinsed and incubated overnight in 10% sucrose (in water) at 4° C., the organoids were dehydrated in graded alcohols (50%, 75%, 96%, 100%), cleared in propylene oxide and embedded in a mixture of Epon 812 and Durcupan (Sigma; polymerization for 3 days at 60° C.). Firstly, semithin sections were cut on Ultrotome Nova (LKB, Sweden) and stained with toluidine blue. Subsequently, ultrathin sections were cut on the same ultramicrotome, collected onto formvar carbon-coated copper grids, counterstained with uranyl acetate and lead citrate and examined under JEOL JEM-1400Plus transmission electron microscope (at 120 kV, JEOL, Japan).

LSEC Functionality Testing

Day 21 organoids were transferred to a 6-well suspension plate, 3 ml/well. To separate wells were added either Alexa Fluor™ 488 AcLDL (Thermofisher, L23380) or fitc-FSA (Gift from Karen Sorensen) both at 2 ug/ml, in the culture medium. These were incubated at 37 C for both 15 and 75 minutes before being washed two times in culture medium and then fixed as described previously. Organoids were then immunostained with endothelial markers as described above.

RNA

Two methods were employed to isolate RNA (i) Cells were collected for RNA isolation from 2D controls by washing the cells once with DPBS−/−, followed by scraping the cells into DPBS−/−. The resulting cell suspension was pelleted by centrifugation at 300×g for 1 minute at room temperature. The supernatant was carefully removed and Trizol (Life Technologies) was added to lyse the cells. For organoids, RNA isolation was performed by removing 2 ml of suspension culture medium from the Erlenmeyer flasks and collecting the organoids by centrifugation at 300×g for 5 minutes at room temperature. The supernatant was carefully removed and the cells were washed with 5 ml of DPBS−/− and repelleted as previously. The DPBS−/− was gently removed and Trizol added to lyse the cells. The Trizol samples were then either processed immediately for RNA isolation according to the manufacturer's instructions or stored at −80° C. for subsequent processing. RNA was quantified using a NanoDrop ND-1000 Spectrophotometer (NanoDrop). (ii) For the vitamin K dependent enzyme analysis total RNA was isolated using the MagMAX™-96 Total RNA Isolation Kit on a MagMAX™ Express-96 Deep Well Magnetic Particle Processor as described by the manufacturer (both from Thermo Fisher Scientific, Waltham, MA, USA).

cDNA Synthesis 500 ng of RNA was used as a template for reverse transcription to cDNA. cDNA synthesis was performed using the High Capacity Reverse Transcriptase Kit (Life Technologies) with random primers, following the manufacturer's instructions for reactions without RNase inhibitor.

Gene Expression Analysis with RT-qPCR

Gene expression was analysed via reverse transcriptase quantitative polymerase chain reaction (RT-qPCR) using TaqMan probes (Life Technologies) and SSO Universal Probes Master Mix (Bio-Rad). For a complete list of probes used in this study, please see Supplementary Table 1. All samples were analysed in triplicate. Data is presented as the average of three independent experiments+/−the standard deviation.

CYP450 Activity and Induction

Analysis of Cytochrome P450 (CYP) basal activity and inducibility was performed as previously described with several modifications for organoid cultures. Briefly the 2D HLCs and organoids were induced from day 20 onwards of differentiation with prototypical CYP450 inducers: for CYP3A4 we cultured with 25 μM Rifampicin and 100 μM Omeprazole for CYP1A2 (Sigma-Aldrich). Prior to starting the inductions the cells/organoids were washed with DPBS−/−4 times to remove hydrocortisone and dexamethasone. After washing the inducers were added to L-15 medium as described above, minus hydrocortisone and dexamethasone. The induction medium was refreshed every 24 hours for 3 days. 72 hours post induction the cells were assayed for CYP1A2 and CYP3A4 activity using the P450-Glo CYP3A4 (Luciferin-PFBE) Cell-based/Biochemical Assay kit (Promega, Cat. no. V8902) and the P450-Glo CYP1A2 Induction/Inhibition Assay kit (Promega, Cat. no. V8422) according to the manufacturer's instructions. Data was normalised to 1 million hepatocytes and is presented as the average of three independent experiments+/−the standard deviation.

Heroin Metabolism

After 21 days differentiation, 50 organoids per well were loaded in triplicate into a 96-well plate and treated with culture media supplemented with 10 μM heroin for 1, 3, 6, and 24 hours. For controls, we used culture media without organoids; these were performed in parallel to measure heroin degradation throughout the experiment. To stop metabolism at each time point the samples were transferred to a new 96-well plate prefilled with formic acid (final conc. 0.1 M) along with internal standards. The samples were centrifuged for 10 minutes at 1000×g at 4° C. The supernatants were transferred to auto-sampler vials and analysed for heroin, morphine, and M3G using an Acquity UPLC system (Waters, Milford, MA) coupled to a Xevo-TQS triple quadrupole mass spectrometer with an electrospray ionization interface (Waters) based on a method previously described 62. Data acquisition, peak integration, and quantification of samples were performed using MassLynx 4.0 SCN509 software (Waters Corp., Milford, MA, USA).

F7 Activity

FVII activity in the cell medium was determined using the Human FVII Chromogenic Activity Kit (Nordic BioSite AB, Taby, Sweden) according to manufacturer's instructions. Primary hepatocytes (Thermo Fisher Scientific) were used as control.

Western Analysis of Factor II

Intracellular levels of FII were determined by western blot (WB). Briefly hepatic organoids were lysed in T-PER™ buffer (Thermo Fisher Scientific) and lysates were collected by centrifugation at 8000×g for 10 minutes. Equal amounts of proteins from lysates were separated by SDS-PAGE using Mini-PROTEAN® TGX™ 10% Precast Gels (Bio-Rad, Hercules, CA, USA) before transfer onto a Sequi-Blot PVDF membrane (Bio-Rad) using the Mini Trans-Blot Electrophoretic Transfer Cell system (Bio-Rad). The membranes were incubated overnight at 4° C. with the primary antibody anti-FII (Novus biologicals, Centennial, CO, USA) or Beta-actin (Sigma Aldrich, Saint Louis, MO, USA). The membranes were washed and then incubated with the appropriate horseradish peroxidase (HRP)-conjugated secondary antibody (Santa Cruz Biotechnology, Dallas, TX, USA) for 1 hour at room temperature. The blots were developed using Radiance Plus chemiluminescent substrate (Azure Biosystems, Dublin, CA, USA) and the signals quantified using the ImageQuant LAS-4000 mini Imager (GE Healthcare, Chicago, IL, USA). Primary hepatocytes were used as control.

Serum Protein Analysis Via ELISA

ELISAs for human Albumin (Bethyl Laboratories Inc cat #E80-129), human Alpha-I-anti-trypsin (Abcam cat #ab108799) and hepatocyte growth factor (Antibodies-online cat #ABIN624992) were used as described by the supplier. Colorimetric readings were taken at the specified wavelength on a SPECTRAmax PLUS 384. Values were derived from standards using appropriate lines of best fit generated on Softmax pro software. For clotting factors organoids were collected by centrifugation for 10 minutes at 300×g and the cell medium was collected. Hepatic organoids were lysed in T-PER™ buffer (ThermoFisher) containing Halt protease and phosphatase inhibitor cocktail 1× (Thermo Fisher cat #78440). FVII and FX antigen (FVIIAg and FXAg) were measured in the cell medium using FVII ELISA kit and FX ELISA kit (Abcam, cat #ab168545 and ab108832) respectively. Primary hepatocytes were used as control. The FVIIAg and FXAg levels (ng/ml) were normalized to $1\times10^6$ cells and the ratio organoid/primary hepatocytes was calculated.

Oleic Acid Accumulation Assay

1 M Oleic acid (Sigma Aldrich) was diluted with NaOH (Sigma Aldrich) and heated at 70° C. for 30 minutes to form a 20 mM Sodium Oleate solution. This was then diluted with a 5% BSA/PBS solution at 37° C. to form a 5 mM Sodium Oleate/BSA complex. This was further diluted to 300 μM in culture media and incubated with organoids for 5 days, changing the media each day. After the fatty acid treatment, the organoids were then incubated with 3.8 μM BODIPY 493/503 (Life Technologies) for 30 minutes in culture media at 37° C., then washed two times with PBS before replacing with fresh culture media containing DRAQ5 (Thermofisher) at 1:1500. Organoids were then imaged on a confocal as described above.

Sample Preparation, Processing and Data Processing of Proteomics Data

Patient Liver Samples

Five patient samples were collected from liver explants from patients undergoing LTX at Oslo University Hospital. The samples were stored in liquid nitrogen. The regional ethics committee approved the use of the patient material (REK 2012-286) in accordance with the Declaration of Helsinki. All participants provided written informed consent.

Samples were processed as follows: the proteins were precipitated with acetone/TCA (Sigma Aldrich). The pellets were resuspended in 8 M Urea in 50 mM NH4HCO3, and the proteins were reduced, alkylated and digested into peptides with trypsin (Promega). The resulting peptides were desalted and concentrated before mass spectrometry by the STAGE-TIP method using a C18 resin disk (3M Empore). Each peptide mixture was analyzed by a nEASY-LC coupled to QExactive Plus (ThermoElectron, Bremen, Germany) with EASY Spray PepMap®RSLC column (C18, 2 μl, 100 Å, 75 μm×25 cm) using a 120 minute LC separation gradient.

The resulting MS raw files were submitted to the MaxQuant software version 1.6.1.0 for protein identification. Carbamidomethyl (C) was set as a fixed modification and acetyl (protein N-term), carbamyl (N-term) and oxidation (M) were set as variable modifications. First search peptide tolerance of 20 ppm and main search error 4.5 ppm were used. Trypsin without proline restriction enzyme option was used, with two allowed mis-cleavages. The minimal unique+razor peptides number was set to 1, and the allowed FDR was 0.01 (1%) for peptide and protein identification. The Uniprot database with 'human' entries (October 2017) was used for the database searches.

Proteins with log 2(intensity)>10 average intensity value were defined as "expressed proteins". Pearson correlation coefficient between liver and organoid was calculated from log 2(intensity) with cor.test function in R. Differential expression of proteins between liver and organoid was defined with more than 2 fold change and $p<0.05$ by two-sided T test. Gene Ontology analysis was conduced with GOstats Bioconductor package[63]. Multiple test correction was performed by Benjamin-Hochberg method with p.adjust function in R.

Library Preparation and Data Processing of scRNAseq scRNA-seq libraries were prepared from the liver organoids at day 48 with Chromium Single Cell 3' Reagent Kits (version 2-10× Genomics) as described previously[64]. Conversion to fastq format, mapping/UMI counting in human genome (hg19) and data aggregation were implemented by mkfastq, count and aggr functions with default parameters in CellRanger software (v2.1.0). Subsequent data processing, such as batch effect normalization, was performed by Seurat software (v3.1.0)65. In each replicate, the feature UMI count was normalized to the total count and multiplied by 10,000. Top 2,000 Highly-Variable Features (HVFs) were then identified by variance stabilizing transformation. Anchor cells across different scRNAseq libraries were identified with HVFs under 20 dimensional spaces from canonical correlation analysis and used for the transformation of multiple scRNAseq datasets into a shared space. Gene expression values were scaled for each gene across all integrated cells and used for principal component analysis (PCA). 20 PCs were further assigned into two dimensional space using Uniform Manifold Approximation and Projection (UMAP) and also used to identify cell clusters. Differentially-expressed genes in each cluster were identified with more than 1.25 fold change and $p<0.05$ by two-sided T test. Overrepresented GO terms were identified by GOstats (v2.24.0)[63]. Multiple test correction was performed by Benjamin-Hochberg method with p.adjust function in R.

The cluster labels were assigned by cell type specific markers and GO terms. Nine out of 22 clusters were first separated by the overrepresentation of "extracellular matrix (GO:0031012)", which is a feature of stellate and endothelial cells. Active (AST) and resting stellate cells (RST) were defined by genes involved in "mitotic nuclear division (GO:0140014)" and its markers (MGP and ELN). Non-stellate clusters were labeled as endothelial cell (EC) and further divided into liver sinusoidal (LSEC) and macrovacular endothelial cells (MVEC) by the absence and presence of vasculogenesis markers (KDR and HAND1)66. Seven out of 13 other clusters were assigned hepatocyte (HEP), cholangiocyte (CHO), Kupffer cell (KPC) and Kupffer precursors (KPP) using the enrichment of GO terms "Cholesterol homeostasis (GO:0042632)", "Keratinization (GO:0031424)", "Phagocytosis (GO:0006909)" and "hematopoietic stem cell differentiation (GO:0060218)", respectively. Five clusters were assigned as peripheral nervous system with the expression of neuronal lineage markers (SOX2 and PAX6) and further divided into neuron (Neu), glia (Glia), neuro progenitor (NPC) and cilia-bearing cell (CBC) with "axon development (GO:0061564)", "glial cell development (GO:0010001)", "mitotic nuclear division (GO:0140014)" and "cilium assembly (GO:0060271)", respectively[64]. We could not identify any unique marker and relevant GO terms in one cluster and labelled it as unknown (UN).

Public transcriptome profiles were downloaded from NCBI Gene Expression Omnibus database. Single-cell transcriptome of the liver organoid from Ouchi et al. (GSE130073)26 and human liver atlas (GSE124395)[27] were merged with our scRNAseq data and plotted into the share UMAP space by Seurat as described above. Clusters, which are mainly composed of CD45+ cells and unique to human liver atlas, were labelled as "other immune cell". Genes were sorted by the difference of average expression of all cells between our and Ouchi et al. liver organoid and used for GSEA (v2.2.2) of REACTOME genes without collapsing gene set[67]. Cell-type specific gene signatures were constructed from bulk RNA-seq in primary hepatocyte (GSE98710, GSE112330 and GSE135619)[11,12] biliary tree stem (GSE73114)[13], stellate (GSE119606)[14] and endothelial cells (GSE114607)[15]. The RNA-seq read was aligned to hg19 human genome by Tophat (v2.2.1) with default parameters[68]. The mapped reads were counted in each gene by HTSeq software (v0.9.0) with options "-s no -f bam"[69].

The factors of technical variations across multiple transcriptome datasets were minimized by RUVs function in RUVSeq (v1.8.0)[70]. Subsequently, differentially expressed genes in each cell type were identified by DESeq2 (v1.14.1). To evaluate the enrichment of the cell-type specific genes, genes were sorted in individual cells by relative expression level to average of all cells and used for GSEAPY software (v0.9.3) with options "--max-size 50000 --min-size 0 -n 1000". Hepatic zone-specific genes were obtained from transcriptome profiles of hepatocyte from laser-microdissected human livers (GSE105127)[18]. After processing the bulk RNA-seq, the zone-specific genes were defined with more than 1.5-fold change and $p<0.05$ by two-sided T test. The enrichment was evaluated by GSEAPY software with pre-ranked genes in individual cells relative to all cells in all hepatocyte clusters.

To investigate transcriptional bias between LSEC and MVEC, cells from EC clusters were ordered in pseudotemporal spaces by Monocle (v2.99.3). Briefly, the monocle object was first constructed from the UMI count matrix for cells in EC clusters and preprocessed according to the instruction. We then replaced data in "normalized_data_projection" and "reducedDimW" with non-transposed and transposed PCA dimensional matrix. In addition, "reducedDimS", "reducedDimA" and "reducedDimK" slot were replaced with transposed UMAP dimensional matrix. The principal graph was learned by learnGraph function with "RGE_method='DDRTree', close_loop=T, prune_graph=F, euclidean_distance_ratio=5". Subsequently, cells are ordered according to the trajectory by orderCells function using MVEC1 as a root cluster. Differentially-expressed genes were identified by differential GeneTest function with the model "~sm.ns(Pseudotime)". Finally. Genes with q<1e-50 were selected as EC ordering-dependent genes and used for GO analysis by GOstats as described above.

Animal Work

Male and female NOD.Cg-Prkdcscid Il2rgtm1Wjl/SzJ (NOD scid gamma, NSG) mice (purchased from The Jackson Laboratory, Bar Harbor, ME, USA) were housed in a Minimal Disease Unit at the animal facility at Oslo University Hospital Rikshospitalet, Oslo, Norway, with a 12 hour light-dark cycle and ad libitum access to water and standard rodent diet. All experiments were performed with co-housed age-matched mice. Mice undergoing surgery were not fasted and were 15 weeks of age at the time of surgery. All animals received human care and the animal experiments were approved the Norwegian National Animal Research Authority (project license no FOTS 19470) and performed according to the European Directive 2010/63/EU, the Animal Research: Reporting of In Vivo Experiments guidelines and The Guide for the Care and Use of Laboratory Animals, 8th edition (NRC 2011, National Academic Press).

Implantation of Human Liver Organoids Under the Rodent Kidney Capsule

Male and female immunodeficient NSG mice were used in this study. The transplantation of the organoids under the kidney capsule or the sham laparotomy was performed as described in 71 with some modifications. In brief, the procedure was performed using proper multimodal analgesia with s.c. administration of a local analgesia (Marcain, 0.07 ml/10 g BW) in combination with s.c. administration of Buprenorfin (0.1 mg/kg) before surgery and general anesthesia with i.p. injection with FD2 (Fentanyl/Domitor/Dormicum) and Antisedan (antagonist) post surgery. Following a sterile preparation of the left flank, a 1.5 cm incision was made midway between the last rib and the iliac crest and approximately 0.5 cm parallel and ventral to the spine[71,72]. The left kidney was slowly externalized through the abdominal incision using sterile cotton swabs, immobilized using non-traumatic forceps and moisturized with warm sterile saline. The injection site was located at the upper lateral side of the kidney, and a 1 ml syringe with a 25G needle containing either the organoid suspension or pure Matrigel (Thermo Fisher Scientific) (sham surgery) was gently pushed under the capsule towards the inferior pole of the kidney in order to avoid perforation and damage to the blood vessels. 50-80 μl organoid suspension or Matrigel matrix was very slowly discharged under the kidney capsule and the needle simultaneously slowly pulled out of the capsule to avoid backflow. Next, the kidney was returned to the body cavity, the abdominal wall closed with suture and the skin incision closed with 7 mm wound clips. Post surgery, the mice were examined daily the first week for normal wound healing, with weight measurements and general well-being, thereafter once a week. Once every week, blood was sampled from the saphena vein for serum markers measurement.

Results

Differentiation of Human Pluripotent Stem Cells to Liver Organoids

We employed a cocktail of small molecule mimetics in a developmentally relevant sequence to mimic in vivo liver development[3-5]. On initiating organoid formation, we observed a rapid aggregation of the hPSCs post single cell seeding, generating aggregates with an average diameter of 116±41 μm, which maintained the pluripotency markers, OCT4, SOX2 and NANOG over 24 hour period. To initiate the developmental programme, aggregates were challenged with a pulse of WNT signalling, via CHIR99021 (CHIR), which lead to an exit from pluripotency and a transition through primitive streak, resulting in aggregates of 128±57 μm (24 hours post CHIR treatment). The WNT signal was removed after 24 hours and by day 2 the aggregates exhibited markers of both mesoderm and definitive endoderm (DE); T, GSC, FOXA2, SOX17, HHEX and CER1 etc. During the initial 2 days of the differentiation we observed a shift in size of the organoids, resulting in mesendodermal aggregates with an average size of 159±46 μm. The mesendodermal aggregates were then subjected to hepatic specification until day 7, the resulting organoids were characterised for the presence of hepatic markers. We observed increased expression of AFP, CEBPa, HNF4a and TTR coinciding with decreased expression of DE markers such as HHEX, SOX17 and GATA4. Expression of the T-box family protein TBX3 was observed, which is a factor involved in hepatic endoderm delamination and subsequent invasion into the adjacent septum transversum mesenchyme (STM), resulting in the mixing of these two germ layers and the formation of the liver bud. Using immunostaining we revealed further characteristics of a mixed lineage liver bud stage. The outer epithelial layer of cells expressed ECAD (CDH1), FOXA2, and CK8, as well as being HNF4u and AFP positive, indicative of an early hepatic phenotype. These epithelial markers were localised to the outer surface and not the core of the organoids.

We characterised the non-epithelial cores of day 7 organoids, where we observed a population of MESP1 positive cells, indicative of mesodermal STM[6]. During development a mesodermal MESP1$^{+}$ population gives rise to mesothelial/sub-mesothelial populations marked by ALCAM and Wilms Tumour (WT1), which in turn give rise to the hepatic stellate cells (HSCs)[6,7]. We also identified ALCAM and Wilms Tumour (WT1) positive populations within the mesenchyme of the organoids, these cells mark the putative mesothelial/sub-mesothelial populations. We then directed these early hepatic organoids to a mature liver-like stage over a 14-day period resulting in the formation of organotypic 3D structures with an average size of 250 μm. The liver organoids exhibited markers of hepatic maturation and tissue-like complexity. Analysis by RT-qPCR clearly demonstrated the expression of hepatic markers such as ALB, A1AT, ASGPR1 as well as genes enriched in the liver such as APOA2, TDO2 and TTR and those involved in xenobiotic metabolism cytochrome P450 (CYP) 3A4 and CYP3A7. Immunofluorescence staining demonstrated that the hepatocytes were located on the surface of the organoids visualised via HNF4α and ALB staining. It is established that organogenesis is initiated when the epithelium interacts with an early mesenchymal population during liver development[8]. This process is driven by a number of paracrine factors including the essential morphogen, hepatocyte growth factor (HGF)[9]. We assessed the production of HGF during the course of the differentiation and noted secretion of HGF increased throughout organoid differentiation. This gives further support to the developmental accuracy of the organoid differentiation as HGF is secreted early in development by the mesenchymal population and later by their derivative, e.g., the hepatic stellate cells (HSCs). This is shown in vivo to drive the expansion and maturation of the liver bud suggesting it potentially fulfils a similar role here in our organoids[10].

Single Cell Transcriptome Analysis of iPSC Derived Liver Organoids

To further dissect the cellular diversity within the liver organoids, we profiled the single-cell transcriptomes of a total of 21,412 cells by scRNAseq. A total of 22 clusters were detected and systematically assigned into liver cell types by unique markers, Gene Ontology (GO) functions and reference transcriptome profiles[11-15]. We identified three hepatocyte-like clusters (HEP1-3) with substantial expression of glycerolipid or cholesterol metabolic genes[16]. In mammalian liver, hepatocytes are hexagonally arranged into hepatic lobules that display a gradient microenvironment of oxygen, nutrients, hormones and secreted proteins from pericentral to periportal zones[17]. To evaluate the spatial heterogeneity of hepatocytes within the liver organoid, we performed Gene Set Enrichment Analysis (GSEA) of gene signatures for human periportal hepatocytes to individual cells in the hepatocyte clusters[18]. The enrichment of periportal gene signatures was significantly different across the three hepatocyte clusters. In particular, the HEP3 cluster was closest to the periportal zone, while HEP1 was more distant suggesting that gene expression zonation of hepatocytes was present in the liver organoids. Next we plotted normalized enrichment scores of periportal gene and showed its significant difference across three HEP clusters. However, at the individual gene level with respect to well-defined zonal genes, these showed low expression and only a few genes were differentially expressed across HEP cluster. Therefore, we demonstrate partial zonation is present via markers differentially expressed across the hepatocyte clusters. For example, several zonation markers such as CYP2E1 and LGR5 were lowly expressed in the liver organoid. We speculate that since our organoids mimic the developing liver and are not yet fully mature i.e. at an early postnatal stage, it is not surprising as full zonation or the acinus architecture is not established at birth and takes many years to fully organise[19].

Next, the endothelial cell (EC)-like clusters were characterized by ECM genes and reference transcriptome annotation and divided into liver sinusoidal (LSEC) and macrovascular endothelial cells (MVEC) by the expression pattern of vascularization markers. To infer continuous EC heterogeneity, we ordered cells from EC clusters along with their gene expression patterns. Six co-expression modules that are transiently expressed with the EC ordering were involved in different cellular events. The modules biased to LSEC included genes related to oxidative reaction and anti-inflammatory response, which are characteristics of the liver sinusoid[20,21]. In contrast, genes involved in smooth muscle and calcium transport were significantly enriched in MVEC-biased gene modules. We next explored LSEC zonation, we mapped gene signatures of LSEC in central and periportal zones (Sonya et al., 2018) and observed no significant differential expression of LSEC markers and gene signatures in the EC clusters, indicating that LSEC zonation is not yet established in our organoid model. This is not too surprising as a study by Liang et al.,[22] only observe pericentral and periportal LSEC zonal populations after day 56 in rodents. In neonates they observed heterogeneity in the pre-mature liver, without clear zonation separation. This is indicative that zonation profiles are being progressively built up during postnatal liver development.

Interestingly, in addition to the above liver cell types, we also identified clusters expressing genes for the development of peripheral nervous system (SOX2, PAX6, STMN2). This is not surprising as the human liver is highly innervated[23], it has also been demonstrated that neural crest cells appear in the epiblast prior to emergence of definitive ectoderm and mesoderm[24,25].

We next examined the consistencies and differences with primary liver and against another liver organoid protocol. Our scRNAseq data were compared against scRNAseq of FACS-sorted human adult liver cell populations, liver organoids derived from another protocol and data from all sources in the shared UMAP space[26,27]. The liver cell types (hepatocytes, HSCs, Kupffer and endothelial cells) in our liver organoid are close to cells derived from the human liver, indicating similar gene expression profiles of these cells between our organoid and primary human liver. The liver organoids from the two different protocols exhibited similar cell composition, but displayed apparent differences in the amount of non-endodermal cell types. For example, our protocol produces high number of endothelial cells, while more than half of cells are committed to hepatocytes in the Ouchi et al. organoids. In addition, peripheral nervous system-like cells were also detectable in the aforementioned study. Our comparative analysis revealed that the liver organoids displayed the generation and maturation of Kupffer cells while not detectable in the Ouchi study. Cells expressing the cell surface marker (MARCO, CD45, CD163, CD16A, LY86 and CD86), complement components (C1QA, C1QB and C1QC) and macrophage regulators (VSIG4 TREM2 and PU.1) were clearly enriched in our protocol. For further comparison we analyzed the preferential pathways between the two protocols. GSEA for REACTOME database revealed that collagen and polyamine metabolic genes are significantly enriched in our protocol. In contrast, cholesterol biosynthetic genes were enriched in Ouchi and colleagues protocol, because of the higher number of hepatocytes in this protocol.

Proteomic Analysis of iPSC Derived Liver Organoids

Above we explored the composition of the organoids at the transcriptome level, next we subjected the organoids to global proteomic analysis. This revealed that 1,842 out of 2,461 detected proteins were expressed in both human primary liver (biopsies from human liver) and in vitro generated liver organoids GO analysis indicated that these enriched proteins were involved in a variety of metabolic pathways and functions including blood coagulation (F2, SERPINC1, SERPING1, FGG, FGA etc.) and glutamine family amino acid metabolic processes (ARG1, ASS1, FAH, GLUL, GFPT1, GOT1; GOT2 etc.). We also used iBAQ plot to illustrate key liver markers in each intensity range. Liver markers such as SOD1 and ALB showed highest expression in both organoid and liver. Other liver markers such as KRT18 (CK18), GSTA2 and SERPINA1 were also expressed in both organoid and liver, but their intensity varied between organoid and liver. GO analysis indicated that similar protein sets were enriched in organoid and liver samples. For example, proteins related to "response to toxic substitution" and "detoxification" were enriched in the highest expression range (25~). Overall, these results support that key liver proteins are commonly expressed in both organoid and liver samples. Next we used unbiased clustering of the proteomic data, clustering was performed to log 2(intensity) value of all-expressed genes (log 2(intensity) >10). We noted a separation of organoid and liver was also robustly observed by various cut-off values (e.g., 10, 15, 20) of the expressed genes. A heatmap shows differentially-expressed proteins between organoids and liver, identifying approximately 200-400 proteins that were differentially expressed. These differences were proteins related to blood cells (e.g. immune response and heme-binding), which were significantly enriched in primary liver. While the organoids, cell cycle and early developmental genes were enriched.

iPSC Derived Liver Organoids Contain Hepatic Parenchymal Cells

Next, immunofluorescence was performed to corroborate both the scRNAseq and proteomic findings of liver-like cellular complexity. Organoids (day 20 to 30) were stained against a battery of typical hepatocyte markers. We verified the presence of hepatocytes by the cytosolic expression of GS and CPS1 along with nuclear expression of hepatic transcription factor HNF4α, which were located on the outer surface of the organoids. The enzymes, GS and CPS1, are involved in the urea cycle and in adult liver are zonally separated[28]. The process of zonation occurs throughout postnatal development with GS being specifically absent from fetal liver hepatocytes[19] and only detectable in the liver parenchyma only after day 2 post partum in humans[19]. The expression of GS in our organoids is thus indicative of a developmental stage surpassing that of fetal liver. This is further reinforced by the expression of the xenobiotic metabolising enzyme CYP2A6, a bona fide marker distinguishing adult from fetal hepatocytes[29] and the expression of ASGP1, a marker of maturity used to purify mature hepatocytes[30]. To further validate our findings, we assessed a panel of highly enriched adult liver genes and observed enrichment of this panel in our organoids.

Another feature of hepatocytes is polarisation, this was first confirmed by the expression of the tight junction protein ZO-1 and the apical export protein MRP2, which are both enriched in bile canaliculi[31,32]. Polarisation was also assessed at the ultrastructural level, revealing features of primary liver tissue, including epithelial cells lining luminal structures arranged in a layer and connected by tight junctions, a feature of the hematobiliary barrier. Along with a polarised epithelial cell morphology with the lumen facing surfaces presenting with numerous microvilli, while the abluminal surface facing the ECM was devoid of microvilli and appeared to be attached to an underlying basal lamina. The other endoderm-derived cell type, the cholangiocytes, are derived from the hepatoblast and line the biliary ducts that drain bile from the liver. We confirmed the presence of cholangiocytes, in cells surrounding lumen, through immunohistochemical staining of CK19 which is present in cholangiocytes and hepatoblasts but is lost in hepatocytes and CK7 which is expressed in vivo from 16-20 weeks post-conception (wpc) in humans[33]. Like the intestinal epithelium, the biliary epithelial cells produce mucins to form a mucus layer. We explored if we could detect the presence of mucus in our organoids. Using Alcian blue staining we observed epithelial cells lining the lumen stained blue indicating the presence of mucopolysaccharides i.e. mucin secreting cells. Interestingly cholangiocytes express neutral and acidic mucins from 23-40 wpc[34].

iPSC Derived Liver Organoids are De Novo Vascularized

Along with the parenchymal cells the human liver is composed of a myriad of non-parenchymal cell types. We first investigated the endothelial populations identified by scRNAseq analysis. We used antibodies to delineate the different endothelial populations. First, we investigated the macrovasculature and observed branched chains and lumen surrounding structures positive for CD31 throughout the organoids. To further validate the presence of vasculature within the organoids, we demonstrated the presence of CD31 positive vascular networks in the organoids. On investigating the volume rendered 3D reconstructs in cross-section, we observed clear lumen with a diameter of 8 μM, which is in the range of capillary lumen (5-10 μm)[35].

We also observed small clusters of $CD34^+$ endothelial structures suggesting continued neo-vascularization from approximately day 20 and beyond and not just the expansion of earlier endothelial structures. In vivo, the microvasculature in the liver bud is acquired from the endothelial cells of the STM, upon its invasion by hepatoblasts. These begin as $CD34^+/CD31^+$ continuous vasculature gradually acquiring liver sinusoidal endothelial cell (LSEC) specific features. In the adult liver LSECs exhibit distinct zonal markers[36], this is recreated in the organoids where the endothelial structures acquire increasing $CD54^+$ expression in proximity to the hepatocyte layer, which suggests that endothelial cell specialisation is potentially a product of the niche. We also investigated the distribution of LYVE1, another marker of LSECs which is associated with their scavenger function[37], this revealed luminal structures within the organoids.

scRNAseq data identified a peripheral neuron population. In order to corroborate these findings we performed immunohistochemistry against TUBB3, we detected TUBB3 positive neurons throughout the organoids. Interestingly the neural crest lineage arises from the pluripotent epiblast, prior to definitive germ layer formation[24,25]. We investigated early points in the differentiation (Day 2 and 7) for the emergence of a neural crest like population. Using RT-qPCR we observed the neural plate border markers PAX3, PAX7, ZIC1 and the neural crest specifiers AP2 and SOX10. At day 7 also we observed the neural crest stem cell marker p75.

iPSC Derived Liver Organoids Contain a Resident Macrophage and Hepatic Stellate Population scRNAseq data identified a discrete population of Kupffer cells, which are the resident macrophage population of the liver and are derived in situ during the hematopoetic phase of liver development in vivo[38,39]. We investigated the presence of Kupffer cells within the organoids using the marker CD68[40], observing a CD68$^+$ population exhibiting typical cytoplasmic granule staining. The endothelial and hematopoetic cells share a common precursor early in development called the hemangioblast. We speculated that the endothelial and Kupffer cell types potentially arise from a common mesodermal population at an early stage of differentiation. To that end we studied early time points in organoid differentiation using RT-qPCR for orchestrators of hematopoietic commitment and observed expression of RUNX1 on day 2, which is essential for hematopoietic commitment. By day 7 we observed the expression of both RUNX1 and GATA2 a player, along with RUNX1, in the early hemangioblast core circuit[41]. We speculate that part of this population will go on to form hematopoietic stem cells, but are not yet specified to a myeloid lineage, from which Kupffer cells would ultimately emerge. Together these data suggest that the mesoderm by virtue of undergoing differentiation adjacent to the endodermal derived cells, facilitate the same role as the mesoderm in liver development in vivo. The scRNAseq analysis identified a putative hepatic stellate cell (HSC) populations via canonical markers such as BGN, CTGF, TPM2, SPARC, IGFBP, TAGLN, DCN, CCL2, COL1A1, etc. In vivo HSCs originate from the undifferentiated mesenchyme[7]. Above ALCAM$^+$, MESP1$^+$ and WT1$^+$ populations were observed in the organoids (potentially a mesothelial/submesothelial equivalent). We speculate that the WT1$^+$ population potentially gives rise to a HSC population. We first assessed αSMA, revealing positive cells seen in close proximity to the hepatocyte population, marked by HNF4α. On closer inspection both HSCs with a star-like morphology, that had long cytoplasmic processes with fine branches, and cells resembling myofibroblasts were observed suggesting quiescent and activated populations. This is corroborated by the scRNAseq data, where both activated and resting populations were detected in UMAP space. We also cannot rule out that the HSCs are fetal in nature, as undifferentiated fetal HSCs express αSMA[42]. One function of HSCs is the production of ECMs including the laminins. Immunohistochemistry using a pan-laminin antibody along with αSMA revealed a close relationship between laminin and HSCs.

iPSC Derived Liver Organoids Display Liver Like Function

The organoids exhibit liver-like transcriptional and protein profiles, as well as a liver-like cellular repertoire. We next investigated the functional attributes of the organoids. The liver has a myriad of functions including the ability to metabolize drugs via the CYP450 enzymes. We assessed the basal and induced levels of CYP1A2 and CYP3A4, which play an important role in metabolism of a range of drugs including caffeine and acetaminophen[43]. The organoids were benchmarked against primary human hepatocytes and a 2D protocol for generating hiPSC derived hepatocytes[4,5]. The basal and induced CYP activity in 2D cultures was similar to previous reports (day 20 of differentiation)[4,5]. The organoids presented with greatly elevated levels of activity for both basal and inducible metabolism at the equivalent time-point. When we compared organoids to primary human hepatocytes we observed robust CYP activity at both basal and induced. In both cases we observed comparable basal levels, while induced we did observe a 4 fold difference in activity for CYP3A4 and approximately a 15 fold for CYP1A2. These levels of activity (basal and induction) were maintained over a 40-day period in the organoids, while activity rapidly declined to almost undetectable levels in 2D culture. We then assessed long-term activity, observing maintenance of basal and inducible activity for 80 days. The signal started to decline from day 50 for CYP3A4 and day 60 for CYP1A2; we speculate that this may be a feature of suboptimal culture conditions for long-term maintenance, possibly due to changing mass transfer conditions within the organoids.

The field of non-CYP450-mediated metabolism has attracted increasing attention as an important player in absorption, distribution, metabolism, and excretion[44]. We investigated liver carboxyl esterases (CES), which are hydrolytic enzymes involved in the metabolism of endogenous esters, ester-containing drugs, pro-drugs and environmental toxicants[45]. The CES enzymes also metabolize a wide range of xenobiotic substrates including heroin, which is metabolized by sequential deacetylation (phase I reaction) to 6-monoacetylmorphine (6-MAM) and morphine. Morphine is then glucuronidated, by a phase II reaction via UDP-glucuronosyltransferase (UGT) to morphine-3-glucuronide (M3G). We tested if organoids supported heroin metabolism by exposure to 10 μM heroin and quantification by UPLC-MS/MS. We also compared organoid metabolism to human liver microsomes and a human S9 fraction (unfractionated microsomes and cytosol. The kinetics of metabolism was slower in the organoids we observed phase I metabolism of heroin by CES to morphine in approximately 6 hours, while the controls produced morphine in approximately 12 minutes. However, phase II metabolism (UGT) to morphine glucuronides was detectable in the organoids and absent in the controls.

The liver is also responsible for the clearance of bilirubin, the end product of heme catabolism, specifically this uptake is carried out by the hepatocytes[46]. We investigated bilirubin uptake via a total bilirubin assay where we demonstrated the effective uptake of unconjugated bilirubin by organoids over a period 48 hours. This is not surprising as scRNAseq data shows the expression of the organic anion transporters in the hepatocyte population. Another essential liver function explored was hepatic urea synthesis, which is required for the removal of excess nitrogen. Above we show the expression of CPS1 and GS enzymes, which are involved in the urea cycle. The organoids on testing against a primary human hepatocyte control, produced and secreted urea into the medium[47].

An important feature of the liver is the production of a plethora of serum proteins, including major plasma proteins, apolipoproteins, coagulation factors and hormones etc. We have demonstrated the production of HGF from our organoids; on inspecting the proteomic datasets numerous serum proteins were identified, including the apolipoproteins (APOA1, APOA4, APOC3 and APOD), hormones (the IGFs) and serine protease inhibitors (SERPING1 and SERPINA1/alpha-1-antitrypsin (A1AT)) etc. Next, we investigated the production and secretion of albumin and A1AT, previously shown to be transcribed and expressed (albumin) in hepatocytes. Both these proteins are secreted from hepatocytes into the circulation in vivo and their secretion into the culture medium was also verified.

The liver also produces and secretes coagulation factors and inhibitors to maintain balanced hemostasis. We investigated if we could detect the expression of these vitamin K-dependent coagulation factors and inhibitors as well as a number of other coagulation factors. The expression of vitamin K-dependent coagulation factors (with the exception of F9 which exhibited very low expression), inhibitors, F8 (expressed in endothelial cells), FBG and anti-thrombin (AT) were all observed. Interestingly the mRNA levels of F10 showed elevated expression compared to the other coagulation factors. We speculate that the elevated levels maybe a feature of the activated HSC population which (indicative of fibrosis) leads to elevated F10[48] and worthy of further investigation. We then investigated protein synthesis and secretion of the vitamin K-dependent coagulation factors with the highest mRNA levels (F7 and F10) by ELISA and the intracellular levels of F2 by western blot. We observed both the production and secretion of F7 and F10 into the cell medium and F2 in hepatic organoids lysates. F7 has a key role in the initiation of blood coagulation so F7 activity was assessed, observing levels comparable to primary human hepatocytes. Finally immunofluorescence demonstrated that F7 localized to the outer epithelial cells, corresponding to the hepatocytes.

A study from Ouchi et al. (2019) demonstrated the accumulation of lipids in a liver organoid model, which displayed a steatohepatitis-like phenotype[25]. We tested whether accumulation of lipids could be established in our organoids. Using the neutral lipid dye Bodipy we established the steady-state level of lipids in untreated organoids, which was low. We next treated organoids with a free fatty acid, which lead to massive lipid accumulation, in enlarged droplets.

We also investigated endothelial cell functionality, we show above that a battery of coagulation factors were expressed in the organoids including F7 in the hepatocytes. F8, an essential component of the hemostatic system, is expressed in the endothelial compartment e.g. the sinusoidal endothelial cells of liver in vivo[49]. To verify F8 was being expressed in the endothelial population of the organoids we performed immunofluorescence, confirming the expression of F8 protein in CD31 positive cells.

The LSEC population are equipped with high-affinity receptors (scavenger) enabling the removal of large molecules and nanoparticles from the blood to maintain blood and tissue homeostasis. The proteomic data also indicated the presence of scavenger receptors (LYVE, LRP1, CD36 and SCARB1) in the organoids. It is also established that LSECs can bind and uptake of acetylated low density lipoprotein (AcLDL) and formaldehyde-treated serum albumin (FSA) a function of the scavenger receptor 10.1016/j.stem.2020.06.007doi.org). On treatment of the organoids with either AcLDL or FSA followed by immunofluorescence staining against the LSEC marker CD54, we observed an association of both AcLDL or FSA with the CD54 LSEC population indicating the binding and uptake of these molecules (FIG. 7N).

Our ECM independent system combined with small molecules is capable of producing 300-500 organoids per ml of culture media, where we routinely produce 10's to 100's of thousands of organoids. Importantly, the cost of production has been reduced by nearly 3 orders compared to conventional 2D approaches. With access to such numbers of organoids we assessed if these could be transplanted and maintained in the kidney capsule of mice. The organoids were introduced into the kidney capsule with or without ECM. Using a human specific albumin assay as readout, we assessed the blood of mice over a 5 week period. No albumin was detectable in the first 96 hours, however we observed secretion of human albumin into the bloodstream of the recipient mice from weeks 1 to 2 post transplantation. This was maintained until the mice were sacrificed at week 5 post-transplantation, while no human albumin was detectable in the sham mice. We then performed immunofluorescence staining on sections from the transplantation-graft/host material to assess the presence and maintenance of cell types upon transplantation. We demonstrate the retention of hepatic populations and structures that were observed in the in vitro cultures. For example, we observed CK7 positive cells surrounding small and large luminal spaces within the transplanted material. Interestingly we observe branching networks of human CD31 positive cells within the transplanted organoid that enter and extend throughout large areas of the kidney parenchyma. We also see the maintenance of both layers and lumen structures positive for HNF4a within the transplanted organoids. We also show cells highly positive for injected dextran within the mesenchyme area of the transplanted organoid, away from the kidney parenchyma. These cells are also positive for albumin. The presence of CD31 (human specific antibody) structures that appear to have anastomosed into the mouse kidney parenchyma further supports the presence of vascularisation within our organoids and ongoing de novo vascularisation.

Discussion

The production of scalable liver-like tissue that exhibits functionally long lived human liver characteristics has remained elusive. Here we describe an approach that can generate massive amounts of functionally mature hPSC derived liver-like organoids. The described protocol is straightforward, efficient, reproducible and organoids can be produced in just 20 days. The organoid differentiation protocol follows a liver-like developmental route, producing organoids that contain a liver-like cellular repertoire including the parenchymal hepatocytes and cholangiocytes. They also contain non-parenchymal cells, hepatic stellate, Kupffer and endothelial populations. Interestingly, further analysis by scRNAseq indicated the presence of both hepatocyte and endothelial zonation. Proteomic analysis also clearly demonstrated a liver like phenotype. scRNAseq data was further confirmed using immunostaining, where we observed the aforementioned cell types. Interestingly, we observed parenchymal cell polarity, which was further supported by electron microscopy. We also confirmed the presence of the non-parenchymal cell types including the stellate and Kupffer cells. Remarkably we also observed de novo vascularization and innervation within our organoids. Finally the organoids present with liver like functional features, which included the production of serum proteins and the coagulation factors. They supported ureagenesis and bilirubin uptake. They are proficient in drug metabolism exhibiting long-term activity, 80 days, with respect to CYP metabolism. They also exhibited non-CYP mediated metabolism using heroin as an exemplar. The organoids have the ability to accumulate fatty acids, presenting with a steatotic like phenotype, potentially providing a model for NAFLD. Finally the organoids can be successfully transplanted into mice where they stably produce human albumin.

Organoids can provide both a unique and powerful model to interrogate disease, understand regeneration and potentially provide the building blocks for bridging therapies for patients waiting for an organ or ultimately provide a replacement organ. A key limitation is scaling, for example in children $10^9$ hepatocytes are required to correct specific metabolic liver function[51], however researchers are currently producing organoids in the 10's to 100's in combination with Matrigel (ECM) and recombinant growth factors, making scaling both a financial and technical bottleneck. Our approach currently produces around 500 organoids per ml of medium used in Erlenmeyer flasks. Therefore, based on our approach we would require culture volumes of 1-3 litres to achieve these numbers. It is also compatible with the controlled production in stirred tank bioreactors as recently demonstrated for cardiac and hematopoietic lineages[52,53] and will provide the field with a game-changing resource to allow the development of clinical as well as screening platforms where the requirement will be in the millions of organoids rather than todays laboratory scale.

More work is required to investigate the potential of these scalable organoids in the context of transplantation for bridging therapies but will potentially provide an important treatment modality for non-reversible acute liver failure[54]. Timing of the transplantation is critical for acute liver failure and many patients receive a graft from a marginal donor instead of waiting for a better offer, which is associated with worse post-transplant outcome[55,56], or succumb to disease without transplantation. Therefore approaches that can improve the condition and prolong the survival of patients with acute liver failure waiting for a liver transplant would increase the number of potential organ offers for a cadaveric graft, reducing the use of marginal donors and even allow transplants to be performed in patients currently not getting a graft offer. We envisage these organoids will provide a powerful tool to address developmental biology in the dish, where we could utilise lineage tracing to investigate the emergence of HSCs and the tissue-resident hematopoietic cells i.e. Kupffer population. Organoid production is scalable at a cost-effective level, but will require standardization in order to provide a platform for drug screening, toxicology, disease modeling, to act as the building blocks to produce liver micro-tissues and potentially scaling to large tissue units.

REFERENCES

1. Trefts, E., Gannon, M. & Wasserman, D. H. The liver. *Curr Biol* 27, R1147-R1151 (2017).
2. Yin, X. et al. Engineering Stem Cell Organoids. *Cell Stem Cell* 18, 25-38 (2016).
3. Sullivan, G. J. et al. Generation of functional human hepatic endoderm from human induced pluripotent stem cells. *Hepatology* 51, 329-335 (2010).
4. Mathapati, S. et al. Small-Molecule-Directed Hepatocyte-Like Cell Differentiation of Human Pluripotent Stem Cells. *Current Protocols in Stem Cell* Biology 38, 1G.6.1-1G.6.18 (2016).
5. Siller, R., Greenhough, S., Naumovska, E. & Sullivan, G. J. Small-molecule-driven hepatocyte differentiation of human pluripotent stem cells. *Stem Cell Reports* 4, 939-952 (2015).
6. Asahina, K., Zhou, B., Pu, W. T. & Tsukamoto, H. Septum transversum-derived mesothelium gives rise to hepatic stellate cells and perivascular mesenchymal cells in developing mouse liver. *Hepatology* 53, 983-995 (2011).
7. Li, Y., Wang, J. & Asahina, K. Mesothelial cells give rise to hepatic stellate cells and myofibroblasts via mesothelial-mesenchymal transition in liver injury. *Proc Natl Acad Sci USA* 110, 2324-2329 (2013).
8. Matsumoto, K., Yoshitomi, H., Rossant, J. & Zaret, K. S. Liver organogenesis promoted by endothelial cells prior to vascular function. *Science* 294, 559-563 (2001).
9. Schmidt, C. et al. Scatter factor/hepatocyte growth factor is essential for liver development. *Nature* 373, 699-702 (1995).
10. Apte, U. et al. Activation of Wnt/beta-catenin pathway during hepatocyte growth factor-induced hepatomegaly in mice. *Hepatology* 44, 992-1002 (2006).
11. Xie, B. et al. A two-step lineage reprogramming strategy to generate functionally competent human hepatocytes from fibroblasts. *Cell Res* 29, 696-710 (2019).
12. Koui, Y. et al. An In Vitro Human Liver Model by iPSC-Derived Parenchymal and Non-parenchymal Cells. *Stem Cell Reports* 9, 490-498 (2017).
13. Oikawa, T. et al. Model of fibrolamellar hepatocellular carcinomas reveals striking enrichment in cancer stem cells. *Nat Commun* 6, 8070 (2015).
14. Martin-Mateos, R. et al. Enhancer of Zeste Homologue 2 Inhibition Attenuates TGF-β Dependent Hepatic Stellate Cell Activation and Liver Fibrosis. *Cell Mol Gastroenterol Hepatol* 7, 197-209 (2019).
15. Marcu, R. et al. Human Organ-Specific Endothelial Cell Heterogeneity. *iScience* 4, 20-35 (2018).
16. Cheng, H. C., Yang, C. M. & Shiao, M. S. Zonation of cholesterol and glycerolipid synthesis in regenerating rat livers. *Hepatology* (*Baltimore, Md.*) 17, 280-286 (1993).
17. Ben-Moshe, S. & Itzkovitz, S. Spatial heterogeneity in the mammalian liver. *Nat Rev Gastroenterol Hepatol* 16, 395-410 (2019).
18. Brosch, M. et al. Epigenomic map of human liver reveals principles of zonated morphogenic and metabolic control. *Nat Commun* 9, 4150 (2018).
19. Moorman, A. F., Vermeulen, J. L., Charles, R. & Lamers, W. H. Localization of ammonia-metabolizing enzymes in human liver: ontogenesis of heterogeneity. *Hepatology* 9, 367-372 (1989).
20. Bissell, D. M., Wang, S. S., Jarnagin, W. R. & Roll, F. J. Cell-specific expression of transforming growth factor-beta in rat liver. Evidence for autocrine regulation of hepatocyte proliferation. *J Clin Invest* 96, 447-455 (1995).
21. Samarasinghe, D. A., Tapner, M. & Farrell, G. C. Role of oxidative stress in hypoxia-reoxygenation injury to cultured rat hepatic sinusoidal endothelial cells. *Hepatology* 31, 160-165 (2000).
22. Liang, Y. et al. Temporal Analyses of Postnatal Liver Development and Maturation by Single Cell Transcriptomics. *bioRxiv,* 2021.2007.2014.451852 (2021).
23. Jensen, K. J., Alpini, G. & Glaser, S. Hepatic Nervous System and Neurobiology of the Liver. *Comprehensive Physiology,* 655-665 (2013).
24. Rosenquist, G. C. Epiblast origin and early migration of neural crest cells in the chick embryo. *Developmental Biology* 87, 201-211 (1981).
25. Prasad, M. S. et al. Blastula stage specification of avian neural crest. *Developmental Biology* 458, 64-74 (2020).
26. Ouchi, R. et al. Modeling Steatohepatitis in Humans with Pluripotent Stem Cell-Derived Organoids. *Cell Metab* 30, 374-384.e376 (2019).
27. Aizarani, N. et al. A human liver cell atlas reveals heterogeneity and epithelial progenitors. *Nature* 572, 199-204 (2019).
28. Poyck, P. P. C. et al. Expression of Glutamine Synthetase and Carbamoylphosphate Synthetase I in a Bioartificial Liver: Markers for the Development of Zonation in vitro. *Cells Tissues Organs* 188, 259-269 (2008).
29. Baxter, M. et al. Phenotypic and functional analyses show stem cell-derived hepatocyte-like cells better mimic fetal rather than adult hepatocytes. *J Hepatol* 62, 581-589 (2015).

30. Peters, D. T. et al. Asialoglycoprotein receptor 1 is a specific cell-surface marker for isolating hepatocytes derived from human pluripotent stem cells. *Development* 143, 1475-1481 (2016).
31. Li, Y., Fanning, A. S., Anderson, J. M. & Lavie, A. Structure of the conserved cytoplasmic C-terminal domain of occludin: identification of the ZO-1 binding surface. *Journal of molecular biology* 352, 151-164 (2005).
32. Orbin, E. et al. Different expression of occludin and ZO-1 in primary and metastatic liver tumors. *Pathol Oncol Res* 14, 299-306 (2008).
33. Desmet, V. J., van Eyken, P. & Sciot, R. Cytokeratins for probing cell lineage relationships in developing liver. *Hepatology* 12, 1249-1251 (1990).
34. Kasprzak, A. & Adamek, A. Mucins: the Old, the New and the Promising Factors in Hepatobiliary Carcinogenesis. *Int J Mol Sci* 20 (2019).
35. Wimmer, R. A. et al. Human blood vessel organoids as a model of diabetic vasculopathy. *Nature* 565, 505-510 (2019).
36. Strauss, O., Phillips, A., Ruggiero, K., Bartlett, A. & Dunbar, P. R. Immunofluorescence identifies distinct subsets of endothelial cells in the human liver. *Sci Rep* 7, 44356 (2017).
37. Kristine, S. K., Simon-Santamaria, J., McCuskey, R. S. & Smedsrød, B. Liver Sinusoidal Endothelial Cells, Vol. 5. (2015).
38. Ginhoux, F. & Jung, S. Monocytes and macrophages: developmental pathways and tissue homeostasis. *Nat Rev Immunol* 14, 392-404 (2014).
39. Hoeffel, G. et al. C-Myb(+) erythro-myeloid progenitor-derived fetal monocytes give rise to adult tissue-resident macrophages. *Immunity* 42, 665-678 (2015).
40. Beljaars, L. et al. Hepatic Localization of Macrophage Phenotypes during Fibrogenesis and Resolution of Fibrosis in Mice and Humans. *Front Immunol* 5, 430 (2014).
41. Wilson, N. K. et al. Combinatorial Transcriptional Control In Blood Stem/Progenitor Cells: Genome-wide Analysis of Ten Major Transcriptional Regulators. *Cell Stem Cell* 7, 532-544 (2010).
42. Geerts, A. On the origin of stellate cells: mesodermal, endodermal or neuro-ectodermal? *Journal of Hepatology* 40, 331-334 (2004).
43. Ogu, C. C. & Maxa, J. L. Drug interactions due to cytochrome P450. *Proc* (*Bayl Univ Med Cent*) 13, 421-423 (2000).
44. Cerny, M. A. Prevalence of Non-Cytochrome P450-Mediated Metabolism in Food and Drug Administration-Approved Oral and Intravenous Drugs: 2006-2015. *Drug Metabolism and Disposition* 44, 1246-1252 (2016).
45. Wang, D. et al. Human carboxylesterases: a comprehensive review. *Acta Pharm Sin B* 8, 699-712 (2018).
46. Cui, Y., König, J., Leier, I., Buchholz, U. & Keppler, D. Hepatic Uptake of Bilirubin and Its Conjugates by the Human Organic Anion Transporter SLC21A6. *Journal of Biological Chemistry* 276, 9626-9630 (2001).
47. Lewis, S. L., Dirksen, S. R., Lewis, S. M., Heitkemper, M. M. L. & Bucher, L. Clinical Companion to Medical-Surgical Nursing: Assessment and Management of Clinical Problems. (Elsevier, 2013).
48. Dhar, A. et al. Thrombin and factor Xa link the coagulation system with liver fibrosis. *BMC Gastroenterology* 18, 60 (2018).
49. Hollestelle, M. J. et al. Tissue distribution of factor VIII gene expression in vivo—a closer look. *Thromb Haemost* 86, 855-861 (2001).
50. Pandey, E., Nour, A. S. & Harris, E. N. Prominent Receptors of Liver Sinusoidal Endothelial Cells in Liver Homeostasis and Disease. *Frontiers in Physiology* 11 (2020).
51. Dhawan, A., Mitry, R. R. & Hughes, R. D. Hepatocyte transplantation for liver-based metabolic disorders. *Journal of inherited metabolic disease* 29, 431-435 (2006).
52. Halloin, C. et al. Continuous WNT Control Enables Advanced hPSC Cardiac Processing and Prognostic Surface Marker Identification in Chemically Defined Suspension Culture. *Stem Cell Reports* 13, 775 (2019).
53. Ackermann, M. et al. Bioreactor-based mass production of human iPSC-derived macrophages enables immunotherapies against bacterial airway infections. *Nat Commun* 9, 5088 (2018).
54. Wendon, J. et al. EASL Clinical Practical Guidelines on the management of acute (fulminant) liver failure. *Journal of Hepatology* 66, 1047-1081 (2017).
55. Bernal, W. et al. Outcome after wait-listing for emergency liver transplantation in acute liver failure: A single centre experience. *Journal of Hepatology* 50, 306-313 (2009).
56. Germani, G. et al. Liver transplantation for acute liver failure in Europe: Outcomes over 20 years from the ELTR database. *Journal of Hepatology* 57, 288-296 (2012).
57. Siller, R. et al. Development of a rapid screen for the endodermal differentiation potential of human pluripotent stem cell lines. *Sci Rep* 6, 37178 (2016).
58. Siller, R. & Sullivan, G. J. Rapid Screening of the Endodermal Differentiation Potential of Human Pluripotent Stem Cells. *Current Protocols in Stem Cell* Biology 43, 1G.7.1-1G.7.23 (2017).
59. Kempf, H. et al. Bulk cell density and Wnt/TGFbeta signalling regulate mesendodermal patterning of human pluripotent stem cells. *Nature Communications* 7, 13602 (2016).
60. Lunova, M. et al. Light-induced modulation of the mitochondrial respiratory chain activity: possibilities and limitations. *Cell Mol Life Sci* 77, 2815-2838 (2020).
61. de Chaumont, F. et al. Icy: an open bioimage informatics platform for extended reproducible research. *Nat Methods* 9, 690-696 (2012).
62. Karinen, R. et al. Determination of heroin and its main metabolites in small sample volumes of whole blood and brain tissue by reversed-phase liquid chromatography-tandem mass spectrometry. *J Anal Toxicol* 33, 345-350 (2009).
63. Falcon, S. & Gentleman, R. Using GOstats to test gene lists for GO term association. *Bioinformatics* 23, 257-258 (2007).
64. Xiang, Y. et al. hESC-Derived Thalamic Organoids Form Reciprocal Projections When Fused with Cortical Organoids. *Cell Stem Cell* 24, 487-497.e487 (2019).
65. Butler, A., Hoffman, P., Smibert, P., Papalexi, E. & Satija, R. Integrating single-cell transcriptomic data across different conditions, technologies, and species. *Nat Biotechnol* 36, 411-420 (2018).
66. Cakir, B. et al. Engineering of human brain organoids with a functional vascular-like system. *Nat Methods* 16, 1169-1175 (2019).

67. Subramanian, A. et al. Gene set enrichment analysis: a knowledge-based approach for interpreting genome-wide expression profiles. *Proc Natl Acad Sci USA* 102, 15545-15550 (2005).

68. Trapnell, C., Pachter, L. & Salzberg, S. L. TopHat: discovering splice junctions with RNA-Seq. *Bioinformatics* 25, 1105-1111 (2009).

69. Anders, S., Pyl, P. T. & Huber, W. HTSeq—a Python framework to work with high-throughput sequencing data. *Bioinformatics* 31, 166-169 (2015).

70. Risso, D., Ngai, J., Speed, T. P. & Dudoit, S. Normalization of RNA-seq data using factor analysis of control genes or samples. *Nat Biotechnol* 32, 896-902 (2014).

71. Zhu, F. et al. A modified method for implantation of pluripotent stem cells under the rodent kidney capsule. *Stem Cells Dev* 23, 2119-2125 (2014).

72. Shultz, L. D. et al. Subcapsular transplantation of tissue in the kidney. *Cold Spring Harb Protoc* 2014, 737-740 (2014).

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

The invention claimed is:

1. An in vitro method for production of liver organoids comprising:

a) suspending vertebrate pluripotent stem cells in a liquid base medium at a density of from 0.5 to 5.0 ml medium per one million pluripotent stem cells;

b) incubating the suspended pluripotent stem cells for 12 to 30 hours under agitation so that the pluripotent stem cells form aggregates;

c) incubating the aggregates from step b) in the presence of a WNT agonist for 12 to 30 hours;

d) incubating the aggregates from step c) in medium without WNT agonist for 12 to 30 hours;

e) incubating the aggregates from step d) in the presence of DMSO for 4 to 9 days; and f) incubating the aggregates from step e) in the presence of a glucocorticoid and an agonist of the hepatocyte growth factor receptor (HGFR) for from 10 to 200 days.

2. The method of claim 1, wherein the liquid base medium in step a) comprises an inhibitor of ROCK-I and/or ROCK-II.

3. The method according to claim 1, wherein the vertebrate cells are mammalian cells or human cells.

4. The method according to claim 1, wherein the medium in step c) comprises insulin.

5. The method according to claim 1, wherein the WNT agonist in step c) is a glycogen synthase kinase (GSK) 3 inhibitor.

6. The method according to claim 5, wherein the glycogen synthase kinase (GSK) 3 inhibitor is CHIR99021, and wherein the medium in step c) comprises from 2 to 6 μM of the CHIR99021.

7. The method according to claim 1, wherein the agonist of the hepatocyte growth factor receptor is N-hexanoic-Tyr, Ile-6 aminohexanoic amide provided at a concentration of 80 to 120 nM.

8. The method according to claim 1, wherein the glucocorticoid in step f) is dexamethasone provided at a concentration of from 80 to 120 nM.

9. The method of claim 1, wherein the organoids express one or more of ALB, A1AT, and ASGPR1.

10. The method of claim 1, wherein the organoids express one or more of APOA2, TDO2 and TTR.

11. The method of claim 1, wherein the organoids express CYP1A2, CYP3A4 and/or CYP3A7.

12. The method of claim 11, wherein the protein(s) CYP1A2 and/or CYP3A4 are expressed in amount sufficient to metabolize caffeine and/or acetaminophen.

13. The method of claim 1, wherein the organoids one or more of the cell surface markers MARCO, CD45, CD163, CD16A, LY86 and CD86.

14. The method of claim 1, wherein the organoids express one or more of the complement components C1QA, C1QB and C1QC.

15. The method of claim 1, wherein the organoids express one or more of the macrophage regulators VSIG4, TREM2 and PU.1.

16. The method of claim 1, wherein the organoids express one or more of BGN, CTGF, TPM2, SPARC, IGFBP, TAGLN, DCN, CCL2, and COL1A1.

17. The method of claim 1, wherein the organoids express carboxyl esterases.

18. The method of claim 17, wherein the carboxyl esterases are expressed in an amount sufficient to metabolize heroin.

19. The method of claim 1, wherein the organoids are able to uptake unconjugated bilirubin.

20. The method of claim 1, wherein the organoids express one or more of the coagulation factors F7, F8, F10, FBG and anti-thrombin (AT).

* * * * *